United States Patent
Lading et al.

(10) Patent No.: US 10,213,117 B2
(45) Date of Patent: Feb. 26, 2019

(54) BLOOD PRESSURE ESTIMATION BASED ON PULSE WAVE VELOCITY

(71) Applicant: QUALCOMM Incorporated, San Diego, CA (US)

(72) Inventors: Lars Lading, Roskilde (DK); David Boettcher Baek, San Diego, CA (US)

(73) Assignee: QUALCOMM Incorporated, San Diego, CA (US)

(*) Notice: Subject to any disclaimer, the term of this patent is extended or adjusted under 35 U.S.C. 154(b) by 197 days.

(21) Appl. No.: 15/215,260

(22) Filed: Jul. 20, 2016

(65) Prior Publication Data

US 2017/0238817 A1 Aug. 24, 2017

Related U.S. Application Data

(60) Provisional application No. 62/297,023, filed on Feb. 18, 2016.

(51) Int. Cl.
| | | |
|---|---|---|
| *A61B 5/04* | (2006.01) | |
| *A61B 5/021* | (2006.01) | |
| *A61B 5/02* | (2006.01) | |
| *A61B 5/024* | (2006.01) | |
| *A61B 5/0285* | (2006.01) | |

(Continued)

(52) U.S. Cl.
CPC ........... *A61B 5/02125* (2013.01); *A61B 5/02* (2013.01); *A61B 5/026* (2013.01); *A61B 5/02007* (2013.01); *A61B 5/0285* (2013.01); *A61B 5/02416* (2013.01); *A61B 5/1076* (2013.01); *A61B 5/681* (2013.01); *A61B 5/6824* (2013.01); *A61B 5/6826* (2013.01); *A61B 5/7253* (2013.01); *A61B 5/7278* (2013.01); *A61B 5/7282* (2013.01); *A61B 2560/0223* (2013.01)

(58) Field of Classification Search
USPC ......................................... 600/300–301, 437
See application file for complete search history.

(56) References Cited

U.S. PATENT DOCUMENTS

| | | |
|---|---|---|
| 7,674,231 B2 | 3/2010 | McCombie et al. |
| 8,167,804 B2 | 5/2012 | Kim et al. |

(Continued)

FOREIGN PATENT DOCUMENTS

WO  WO-2015077838 A1  6/2015

OTHER PUBLICATIONS

International Search Report and Written Opinion—PCT/US2017/013965—ISA/EPO—dated May 3, 2017.

*Primary Examiner* — Nicole F Johnson
(74) *Attorney, Agent, or Firm* — Bala Ramasamy; Weaver Austin Villeneuve & Sampson LLP

(57) ABSTRACT

One aspect of the subject matter described in this disclosure can be implemented in a device capable of estimating blood pressure. The device includes two or more sensors capable of performing measurements along an artery. The device also includes at least one processing unit coupled with the two or more sensors. The processing unit is capable of accessing one or more parameters including a stress-strain parameter based on a hydrostatic pressure calibration. The processing unit also is capable of determining a pulse transit time (PTT) based on the measurements, and determining a pulse wave velocity (PWV) based on the PTT. The processing unit is further capable of determining a blood pressure based on the PWV and the stress-strain parameter.

24 Claims, 18 Drawing Sheets

(51) Int. Cl.
*A61B 5/00* (2006.01)
*A61B 5/026* (2006.01)
*A61B 5/107* (2006.01)

(56) References Cited

U.S. PATENT DOCUMENTS

| | | |
|---|---|---|
| 8,313,439 B2 | 11/2012 | McCombie et al. |
| 8,672,854 B2 | 3/2014 | McCombie et al. |
| 2011/0152699 A1 | 6/2011 | Cho |
| 2013/0296723 A1 | 11/2013 | Cho et al. |
| 2014/0296677 A1 | 10/2014 | McEowen |
| 2015/0327786 A1* | 11/2015 | Lading ................ A61B 5/0082 600/437 |
| 2015/0366469 A1 | 12/2015 | Harris et al. |

* cited by examiner

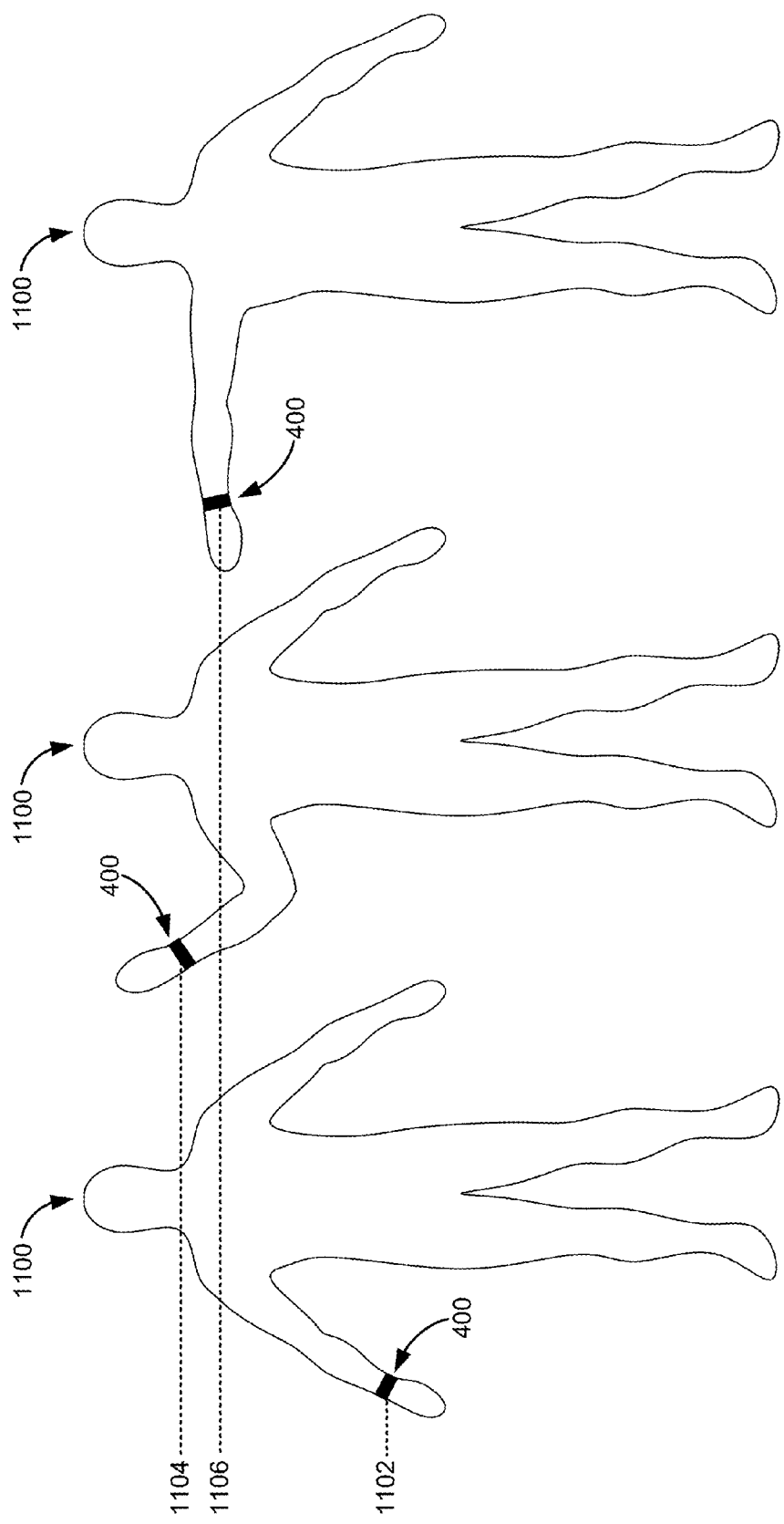

BLOOD PRESSURE ESTIMATION BASED ON PULSE WAVE VELOCITY

PRIORITY CLAIM

This application claims the benefit of priority under 35 U.S.C. § 119(e) to U.S. Provisional Patent Application Ser. No. 62/297,023 titled "BLOOD PRESSURE ESTIMATION BASED ON PULSE WAVE VELOCITY" by Lading et al. and filed on 18 Feb. 2016, which is hereby incorporated by reference herein in its entirety and for all purposes.

TECHNICAL FIELD

This disclosure relates generally to sensing devices for fluid flow systems, and more particularly, to ambulatory monitoring devices capable of use in estimating cardiovascular characteristics based on measurements of an arterial distension waveform.

DESCRIPTION OF RELATED TECHNOLOGY

A variety of different sensing technologies and algorithms are being investigated for use in various biomedical applications, including health and wellness monitoring. This push is partly a result of the limitations in the usability of traditional measuring devices for continuous, noninvasive and ambulatory monitoring. For example, a sphygmomanometer is an example of a traditional blood pressure monitoring device that utilizes an inflatable cuff to apply a counter pressure to a region of interest (for example, around an upper arm of a subject). The pressure exerted by the inflatable cuff is designed to restrict arterial flow in order to provide a measurement of systolic and diastolic pressure. Such traditional sphygmomanometers inherently affect the physiological state of the subject, which can introduce an error in the blood pressure measurements. Such sphygmomanometers also can affect the psychological state of the subject, which can manifest itself in a physiological state change, and thus, introduce an error in the blood pressure measurements. For example, such devices are often used primarily on isolated occasions, for example, when a subject visits a doctor's office or is being treated in a hospital setting. Naturally, some subjects experience anxiety during such occasions, and this anxiety can influence (for example, increase) the user's blood pressure as well as heart rate.

Additionally, such traditional sphygmomanometers are not portable in the sense that they cannot be worn without restriction of ambulatory movement, or are otherwise inhibiting, interfering or distracting. For these and other reasons, such devices do not provide an accurate estimation or "picture" of blood pressure, and a user's health in general, over time. While implanted or otherwise invasive devices may provide better estimates of blood pressure over time, such invasive devices generally involve greater risk than noninvasive devices and are generally not suitable for ambulatory use.

SUMMARY

The systems, methods and devices of this disclosure each have several aspects, no single one of which is solely responsible for the desirable attributes disclosed herein.

One aspect of the subject matter described in this disclosure can be implemented in a device capable of estimating blood pressure. The device includes two or more sensors capable of performing measurements along an artery of a subject. The device also includes at least one processing unit coupled with the two or more sensors. The processing unit is capable of accessing one or more parameters including a stress-strain parameter based on a hydrostatic pressure calibration. The processing unit also is capable of determining a pulse transit time (PTT) based on the measurements performed by the two or more sensors, and determining a pulse wave velocity (PWV) based on the PTT. The processing unit is further capable of determining a blood pressure in the artery based on the PWV and the stress-strain parameter.

The two or more sensors can include at least a first sensor and a second sensor. In some implementations, the determination of the PTT based on the measurements performed by the two or more sensors includes determining a first temporal location of a pulse propagating through the artery based on the measurements performed by the first sensor, determining a second temporal location of the pulse based on the measurements performed by the second sensor, and determining the PTT based on the first temporal location and the second temporal location. In some implementations, the device further includes a wearable housing that encompasses at least portions of the first sensor and the second sensor. The wearable housing provides a fixed distance of separation between the first sensor and the second sensor. In such implementations, the processing unit is capable of determining the PWV based on the fixed distance of separation and the PTT. In some implementations, a magnitude of the fixed distance of separation is less than about 5 centimeters (cm).

In some implementations, the determination of the blood pressure in the artery based on the PWV and the stress-strain parameter includes determining the blood pressure based on a first relationship between blood pressure and PWV that includes the stress-strain parameter and no other stress-strain parameters.

In some implementations, the at least one processing unit is also capable of performing the hydrostatic pressure calibration to obtain the stress-strain parameter. In some implementations, the device further includes at least one elevation sensor coupled with the at least one processing unit and capable of performing elevation measurements associated with a relative or an absolute elevation of the device. The at least one processing unit is capable of determining the stress-strain parameter based on a hydrostatic pressure difference between a first elevation and a second elevation.

In some implementations, the device further includes a signal processor capable of performing one or more signal processing operations on the measurements performed by the two or more sensors to provide processed arterial distension data. In some implementations, one or more of the one or more signal processing operations includes applying a nonlinear function to provide the processed arterial distension data.

In some implementations, the determination of the PTT based on the measurements performed by the two or more sensors includes performing a correlation operation based on the measurements performed by the first sensor at the first physical location and based on the measurements performed by the second sensor at the second physical location. In some such implementations, the determination of the PTT also includes determining correlation data as a function of time delay based on the correlation operation. In some such implementations, the determination of the PTT further includes determining a time delay associated with an approximate maximum of the correlation data, and determining the PTT based on the determined time delay.

Another aspect of the subject matter described in this disclosure can be implemented in a device capable of estimating blood pressure. The device includes one or more sensors capable of performing measurements along an artery of a subject. The device further includes at least one processing unit coupled to the one or more sensors. The processing unit is capable of accessing one or more parameters including a stress-strain parameter based on a hydrostatic pressure calibration. The processing unit also is capable of determining blood flow through the artery based on the measurements from the one or more sensors. The processing unit also is capable of determining a cross-sectional area of the artery based on the measurements from the one or more sensors. The processing unit is further capable of determining a pulse wave velocity (PWV) based on the blood flow and the cross-sectional area, and of determining a blood pressure in the artery based on the PWV and the stress-strain parameter.

In some implementations, the determination of the PWV based on the blood flow and the cross-sectional area includes determining a derivative estimate of the blood flow as a function of the cross-sectional area. In some implementations, the determination of the PWV based on the blood flow and the cross-sectional area further includes determining a value of a constant portion of the derivative estimate.

Another aspect of the subject matter described in this disclosure can be implemented in a method of estimating blood pressure. The method includes performing measurements of arterial distension by two or more sensors positioned along an artery of a subject. The method also includes determining a pulse transit time (PTT) based on the measurements, and determining a pulse wave velocity (PWV) based on the PTT. The method also includes accessing one or more parameters including a stress-strain parameter based on a hydrostatic pressure calibration. The method further includes determining a blood pressure in the artery based on the PWV and the stress-strain parameter.

The two or more sensors can include at least a first sensor and a second sensor. In some implementations, determining the PTT based on the measurements performed by the two or more sensors includes determining a first temporal location of a pulse propagating through the artery based on the measurements performed by the first sensor, determining a second temporal location of the pulse based on the measurements performed by the second sensor, and determining the PTT based on the first temporal location and the second temporal location. In some implementations, the first sensor and the second sensor are encompassed at least partially by a wearable housing, the wearable housing providing a fixed distance of separation between the first sensor and the second sensor.

In some implementations, determining the blood pressure in the artery based on the PWV and the stress-strain parameter includes determining the blood pressure based on a first relationship between blood pressure and PWV that includes the stress-strain parameter and no other stress-strain parameters.

In some implementations, the method further includes performing the hydrostatic pressure calibration to obtain the stress-strain parameter. In some such implementations, the method includes performing elevation measurements associated with a relative or an absolute elevation, and determining the stress-strain parameter based on a hydrostatic pressure difference between a first elevation and a second elevation.

In some implementations, the method further includes applying a nonlinear function to the measurements performed by the two or more sensors to provide processed arterial distension data.

In some implementations, the determining of the PTT based on the measurements performed by the two or more sensors includes performing a correlation operation based on the measurements performed by the first sensor at the first physical location and based on the measurements performed by the second sensor at the second physical location. In some such implementations, the determining of the PTT also includes determining correlation data as a function of time delay based on the correlation operation. In some such implementations, the determining of the PTT further includes determining a time delay associated with an approximate maximum of the correlation data, and determining the PTT based on the determined time delay.

Another aspect of the subject matter described in this disclosure can be implemented in a method of estimating blood pressure. The method includes performing measurements of arterial distension by one or more sensors positioned along an artery of a subject. The method also includes accessing one or more parameters including a stress-strain parameter based on a hydrostatic pressure calibration. The method also includes determining a blood flow through the artery based on the measurements. The method also includes determining a cross-sectional area of the artery based on the measurements. The method also includes determining a pulse wave velocity (PWV) based on the blood flow and the cross-sectional area. The method further includes determining a blood pressure in the artery based on the PWV and the stress-strain parameter.

In some implementations, the determining of the PWV based on the blood flow and the cross-sectional area includes determining a derivative estimate of the blood flow as a function of the cross-sectional area. In some such implementations, the determining of the PWV based on the blood flow and the cross-sectional area further includes determining a value of a constant portion of the derivative estimate.

Details of one or more implementations of the subject matter described in this disclosure are set forth in the accompanying drawings and the description below. Other features, aspects, and advantages will become apparent from the description, the drawings and the claims. Note that the relative dimensions of the following figures may not be drawn to scale.

BRIEF DESCRIPTION OF THE DRAWINGS

FIG. 11A shows a diagrammatic representation of a standing subject wearing an ambulatory monitoring device on a wrist positioned at an elevation below the subject's heart.

FIG. 11B shows a diagrammatic representation of a standing subject wearing an ambulatory monitoring device on a wrist positioned at an elevation above the subject's heart.

FIG. 11C shows a diagrammatic representation of a standing subject wearing an ambulatory monitoring device on a wrist positioned at an elevation approximately level with the subject's heart.

Like reference numbers and designations in the various drawings indicate like elements.

DETAILED DESCRIPTION

Figure 1:
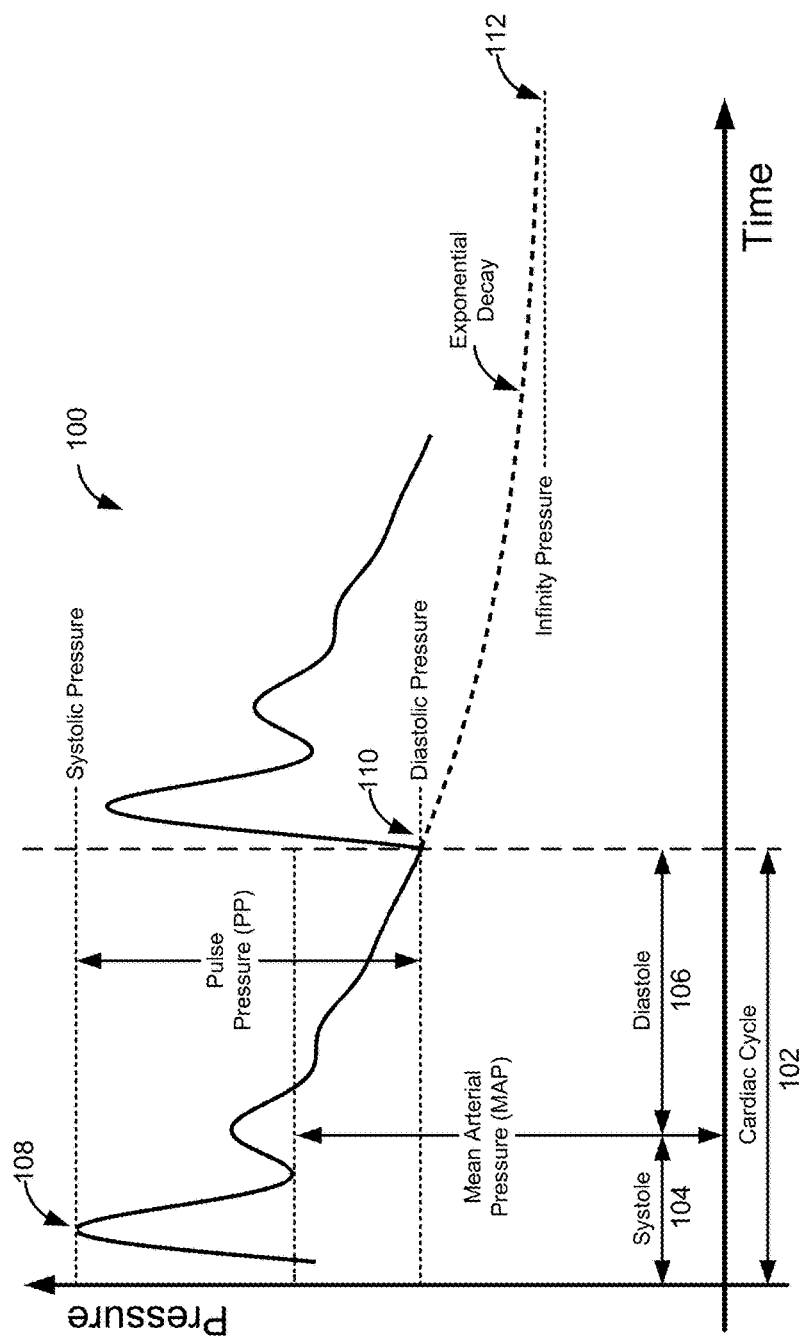
FIG. 1 shows a plot of a blood pressure signal in an example artery versus time during an example cardiac cycle.

The following description is directed to certain implementations for the purposes of describing various aspects of this disclosure. However, a person having ordinary skill in the art will readily recognize that the teachings herein can be applied in a multitude of different ways. Some of the concepts and examples provided in this disclosure are especially applicable to blood pressure monitoring applications. However, some implementations also may be applicable to other types of biological sensing applications, as well as to other fluid flow systems. Thus, the teachings are not intended to be limited to the specific implementations depicted and described with reference to the drawings; rather, the teachings have wide applicability as will be readily apparent to persons having ordinary skill in the art.

Also of note, the conjunction "or" as used herein is intended in the inclusive sense where appropriate unless otherwise indicated; that is, the phrase "A, B or C" is intended to include the possibilities of A individually; B individually; C individually; A and B and not C; B and C and not A; A and C and not B; and A and B and C. Similarly, a phrase referring to "at least one of" a list of items refers to any combination of those items, including single members. As an example, the phrase "at least one of A, B, or C" is intended to cover the possibilities of at least one of A; at least one of B; at least one of C; at least one of A and at least one of B; at least one of B and at least one of C; at least one of A and at least one of C; and at least one of A, at least one of B and at least one of C.

This disclosure relates generally to devices, systems and methods for estimating various characteristics of interest (also referred to herein as "properties" or "signals") in a fluid flow system, and in particular, a pulsating fluid flow system. Such pulsating fluid flow systems can be naturally occurring or designed or constructed by man. Various implementations are more particularly directed or applicable to devices, systems and methods for estimating various biological characteristics including, for example, dynamic or time-varying cardiovascular characteristics such as blood pressure, based on measurements of an arterial distension waveform. Some implementations more specifically relate to devices, systems and methods for estimating blood pressure based on pulse wave velocity (PWV) estimates associated with arterial flow or pressure pulses propagating through the arterial system. In some implementations, the PWV estimates are calculated based on pulse transit time (PTT) estimates. In some implementations, the PTT estimates are calculated based on measurements associated with the time-varying arterial distension of an artery obtained by two or more sensors positioned along the artery.

Some implementations further relate to calibration and validation techniques, and more specifically, to calibration techniques based on hydrostatic pressure measurements. In particular, such calibration techniques do not require external reference devices or the use of known or inferred person-specific attributes. In some implementations, the calibration techniques provide full initial calibration as well as continued or regular updating of calibration subsequent to the initial calibration. Such initial and subsequent updating of calibration enables accurate blood pressure estimation, as well as the accurate monitoring of other cardiovascular system characteristics, even as cardiovascular properties change over time, for example, as the elastic properties of the arterial walls dilate or contract or otherwise become more elastic or less elastic (more stiff).

Some implementations further relate to nonlinear signal processing techniques including, for example, nonlinear filtering and temporal localization techniques for isolating pulses associated with dominant propagating wave modes and for identifying locations associated with particular features or characteristics of such pulses. For example, some implementations include applying nonlinear functions to raw or processed sensor data. Some implementations also can involve correlating raw or processed sensor data and identifying maxima of such correlated data. Some specific implementations incorporate Hilbert filtering, a nonlinear filtering technique involving the use of a Hilbert transform.

Particular implementations of the subject matter described in this disclosure can be implemented to realize one or more of the following potential advantages. Some implementations provide full initial calibration and continued updating or validation of calibration without the use of an external reference device or any externally applied counter pressure. For example, the updating of calibration during regular operation can be desirable, and even critical, in circumstances in which the arterial properties change over time, for example, as the smooth muscles of the arterial walls contract (tighten) or dilate (relax). Some implementations of the ambulatory monitoring devices described herein also are designed to consume relatively little power enabling continuous wearing and monitoring of a biological signal of interest, such as an arterial distension waveform or a blood pressure, over extended durations of time (for example, hours, days, weeks or even a month or more) without external calibration, recharging or other interruption. It is also noted that PWV in its own right can be the basis for some types of cardiovascular diagnostics. Continuous monitoring provides greater prognostic and diagnostic value than isolated measurements, for example, obtained in a hospital or doctor's office setting.

Some implementations of the ambulatory monitoring devices described herein also are designed with small form factors and with housings that can be coupled to a subject (also referred to herein as a "patient," "person" or "user") so as to be wearable, noninvasive, and nonrestrictive of ambulatory use. In other words, some implementations of the ambulatory monitoring devices described herein do not restrict the free uninhibited motion of a subject's arms or legs enabling continuous or periodic monitoring of cardiovascular characteristics such as blood pressure even as the subject is mobile or otherwise engaged in a physical activity. Not only do such devices not interfere with the subject's daily or other desired activities, they also may encourage continuous wearing by virtue of such non-interference. In some implementations, it can further be desirable that the subject has no notion about when the sensing device(s) of the ambulatory monitoring device is actually performing measurements.

As used herein, the term "pulse pressure" refers to the difference between the systolic pressure and the diastolic pressure for a given cardiac cycle. Pulse pressure is generally not affected by local changes in the hydrostatic pressure in an artery in the peripheral regions of the body of a subject. As used herein, the term "transmural pressure" refers to the pressure difference between the pressure inside a particular artery and the pressure directly outside the artery at a particular time and at a particular location along the artery. Unlike the pulse pressure, the transmural pressure depends on hydrostatic pressure. For example, if a sensing device is coupled with a wrist of a subject, changing the elevation of the wrist can cause significant changes in the transmural pressure measured at the wrist, while the pulse pressure will generally be relatively unaffected (assuming the state of the subject is otherwise unchanged). As used herein, the term "absolute arterial pressure" refers to the actual pressure in a particular artery at a particular location along the artery at a particular time. Typically, the absolute arterial pressure is relatively consistent with the transmural pressure so long as no significant external pressure is applied to the artery (such as from a counter pressure applied by an inflatable cuff or other external device). For many intents and purposes, the transmural pressure may be presumed to be approximately equal to the absolute arterial pressure, and as such, the terms "absolute arterial pressure" and "transmural pressure" are used interchangeably hereinafter where appropriate unless otherwise noted. As used herein, the term "blood pressure" is a general term referring to a pressure in the arterial system of a subject. As such, the terms transmural pressure, absolute arterial pressure, pulse pressure, systolic pressure and diastolic pressure all may referred to hereinafter generally as blood pressure.

Pulse Wave Velocity and Blood Pressure

When fluid is injected into a vessel over a relatively short duration of time, the injection will typically generate several propagating wave modes of pressure and fluid motion. Which of the modes is dominant depends on the properties of the vessel and the fluid. In the context of the cardiovascular system, propagating wave modes—referred to hereinafter as "pulses"—are generated responsive to the contraction of the left ventricle of the heart and the accompanying injection of blood into the arterial system. More specifically, the left ventricle injects blood into the aorta from which all of the remaining arteries of the arterial system branch. In this context, the fluid—blood—can be modeled as incompressible, while the vessel—the arterial walls of an artery—can be modeled as elastic. The dominant propagating wave mode along a typical artery is the propagating deformation of the arterial walls of the artery, referred to hereinafter as an arterial distension waveform or as an arterial distension signal (as used herein, the arterial distension signal also can refer to measurements of the arterial distension waveforms obtained for a series or sequence of pulses over an extended duration of time).

The time-varying nature of the arterial distension waveform results from the flow and pressure pulses caused by the subject's heartbeat. In some implementations, a cardiovascular characteristic referred to as the pulse wave velocity (PWV) is estimated based on measurements obtained for the pulses. As used herein, PWV refers generally to the velocity of propagating flow or pressure pulses (also referred to herein as flow or pressure waves) in the cardiovascular system, and in particular, the arterial system. In different terms, the PWV can refer to the speed of the propagation of the variation in arterial diameter resulting from a subject's heartbeat, that is, the speed at which the arterial distension waveform envelope propagates. As used herein, reference to a pulse can encompass a flow pulse or a pressure pulse—both are physical descriptions of the same underlying response of the arterial system. However, while flow pulses and pressure pulses propagate with the same velocities, the pulse shapes (the particular shapes of the waveforms) of the two types of pulses can generally be different. This difference exists because of the nonlinear relationship between the arterial distension signal caused by the flow pulses and the time-varying pressure variation associated with the pressure pulses; the nonlinearity exists in part because the elasticity of the arterial walls decreases with increasing distension. Although the term "arterial distension signal" is sometimes strictly used with reference to flow pulses, as used herein the arterial distension signal may refer to the arterial distension waveform associated with either flow pulses or pressure pulses.

FIG. 1 shows a plot 100 of a blood pressure signal in an example artery versus time during an example cardiac cycle. Although the plot 100 is a plot of blood pressure versus time, the plot 100 also is indicative of the arterial distension waveform. As indicated above, a plot of blood flow versus time would exhibit similar features as the plot 100 of blood pressure versus time, although the specific shapes of the features would be slightly different. As a person of ordinary skill in the art will appreciate, each cardiac cycle 102 includes both a systolic phase ("ventricular systole") 104, during which the left ventricle of the heart contracts and pumps blood into the arterial system, and a diastolic phase ("ventricular diastole") 106, during which the left ventricle relaxes and fills with blood in preparation for the next systolic phase. Because each cardiac cycle 102 yields a respective pressure pulse, the arterial distension waveform associated with each pressure pulse also includes features characteristic of the systolic and diastolic phases. For example, the systolic phase 104 characteristically includes a rapid rise of the pressure culminating in a local maximum or peak 108 (the "systolic pressure") responsive to the injection of blood from the left ventricle during the given cardiac cycle 102. The diastolic phase 106, on the contrary, characteristically includes a marked drop in blood pressure culminating in a local minimum 110 (the "diastolic pressure") during the given cardiac cycle 102 as a consequence of the relaxation of the left ventricle. In fact, the ending portion of the diastolic phase 106 can generally be characterized by an exponentially decaying blood pressure that asymptotically approaches a pressure 112 (referred to herein as the "infinity pressure") lower than the typical diastolic pressure (the blood pressure never reaches the infinity pressure because the systolic phase of the next cardiac cycle interrupts the exponential decay as shown).

Figure 2:
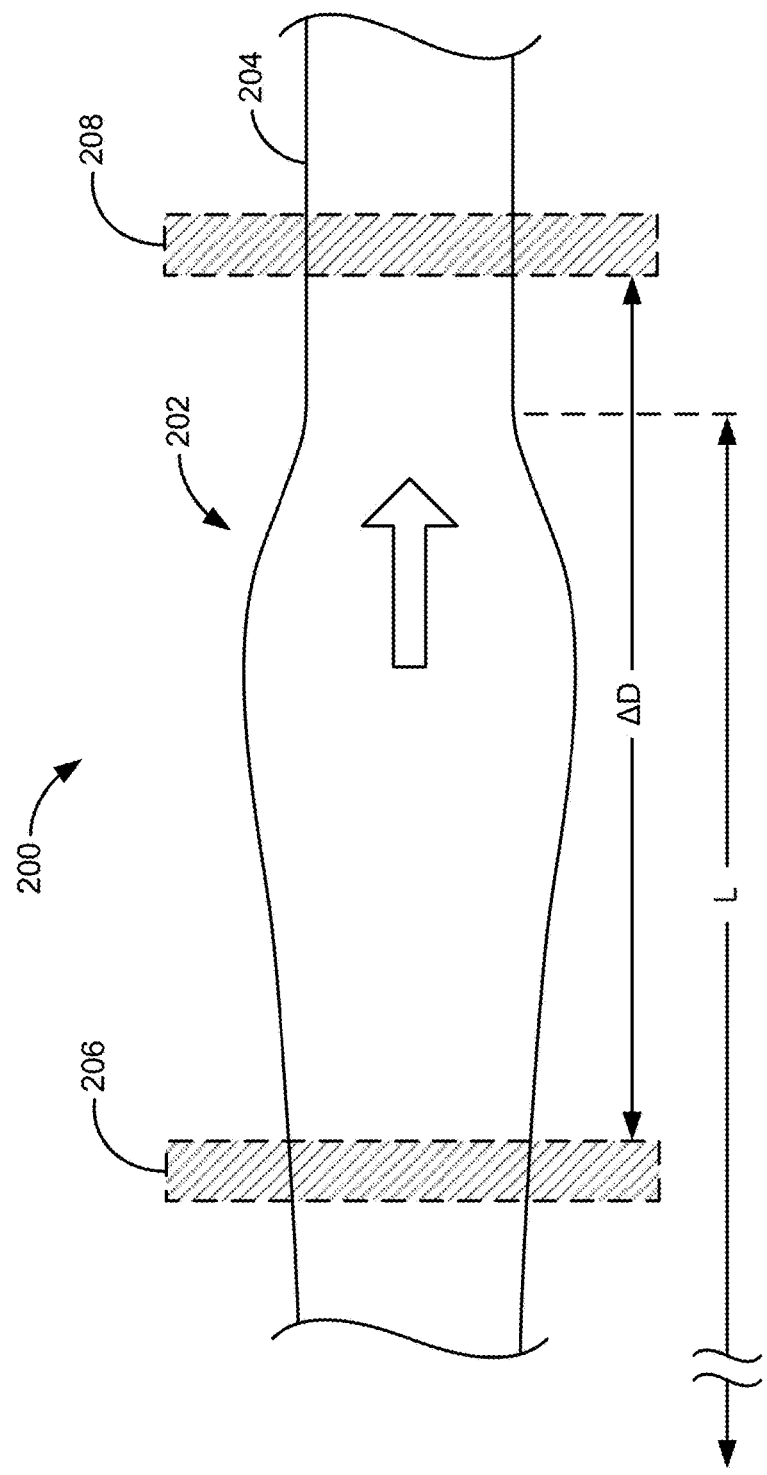
FIG. 2 shows a cross-sectional side view of a diagrammatic representation of a portion of an artery through which a pulse is propagating.

FIG. 2 shows a cross-sectional side view of a diagrammatic representation of a portion of an artery 200 through which a pulse 202 is propagating. The block arrow in FIG. 2 shows the direction of blood flow and pulse propagation. As diagrammatically shown, the propagating pulse 202 causes strain in the arterial walls 204, which is manifested in the form of an enlargement in the diameter (and consequently the cross-sectional area) of the arterial walls—referred to as "distension." The spatial length L of an actual propagating pulse along an artery (along the direction of blood flow) is typically comparable to the length of a limb, such as the distance from a subject's shoulder to the subject's wrist or finger, and is generally less than one meter (m). However, the length L of a propagating pulse can vary considerably from subject to subject, and for a given subject, can vary significantly over durations of time depending on various factors. The spatial length L of a pulse will generally decrease with increasing distance from the heart until the pulse reaches capillaries.

As described above, some particular implementations relate to devices, systems and methods for estimating blood pressure or other cardiovascular characteristics based on estimates of an arterial distension waveform. The terms "estimating," "measuring," "calculating," "inferring," "deducing," "evaluating," "determining" and "monitoring" may be used interchangeably herein where appropriate unless otherwise indicated. Similarly, derivations from the roots of these terms also are used interchangeably where appropriate; for example, the terms "estimate," "measurement," "calculation," "inference" and "determination" also are used interchangeably herein. In some implementations, the PWV of a propagating pulse is estimated by measuring the pulse transit time (PTT) of the pulse as it propagates from a first physical location along an artery to another more distal second physical location along the artery. Assuming that the physical distance ΔD between the first and the second physical locations is ascertainable, the PWV can be estimated as the quotient of the physical spatial distance ΔD traveled by the pulse divided by the temporal distance PTT the pulse takes in traversing the physical spatial distance ΔD.

Generally, a first sensor positioned at the first physical location is used to determine a starting time (also referred to herein as a "first temporal location") at which point the pulse arrives at or propagates through the first physical location. A second sensor at the second physical location is used to determine an ending time (also referred to herein as a "second temporal location") at which point the pulse arrives at or propagates through the second physical location and continues through the remainder of the arterial branch. The PTT represents the temporal distance (or time difference) between the first and the second temporal locations (the starting and the ending times).

The fact that measurements of the arterial distension waveform are performed at two different physical locations implies that the estimated PWV inevitably represents an average over the entire path distance ΔD through which the pulse propagates between the first physical location and the second physical location. More specifically, the PWV generally depends on a number of factors including the density of the blood ρ, the stiffness E of the arterial wall (or inversely the elasticity), the arterial diameter, the thickness of the arterial wall, and the blood pressure. Because both the arterial wall elasticity and baseline resting diameter (for example, the diameter at the end of the ventricular diastole period) vary significantly throughout the arterial system, PWV estimates obtained from PTT measurements are inherently average values (averaged over the entire path length ΔD between the two locations where the measurements are performed).

In traditional methods for obtaining PWV, the starting time of the pulse has been obtained at the heart using an electrocardiogram (ECG) sensor, which detects electrical signals from the heart. For example, the starting time can be estimated based on the QRS complex—an electrical signal characteristic of the electrical stimulation of the heart ventricles. In such approaches, the ending time of the pulse is typically obtained using a different sensor positioned at a second location (for example, a finger). As a person having ordinary skill in the art will appreciate, there are numerous arterial discontinuities, branches, and variations along the entire path length from the heart to the finger. The PWV can change by as much as or more than an order of magnitude along various stretches of the entire path length from the heart to the finger. As such, PWV estimates based on such long path lengths are unreliable.

In various implementations described herein, PTT estimates are obtained based on measurements (also referred to as "arterial distension data" or more generally as "sensor data") associated with an arterial distension signal obtained by each of a first arterial distension sensor 206 and a second arterial distension sensor 208 proximate first and second physical locations, respectively, along an artery of interest. In some particular implementations, the first arterial distension sensor 206 and the second arterial distension sensor 208 are advantageously positioned proximate first and second physical locations between which arterial properties of the artery of interest, such as wall elasticity and diameter, can be considered or assumed to be relatively constant. In this way, the PWV calculated based on the PTT estimate is more representative of the actual PWV along the particular segment of the artery. In turn, the blood pressure P estimated based on the PWV is more representative of the true blood pressure. In some implementations, the magnitude of the distance ΔD of separation between the first arterial distension sensor 206 and the second arterial distension sensor 208 (and consequently the distance between the first and the second locations along the artery) can be in the range of about 1 centimeter (cm) to tens of centimeters—long enough to distinguish the arrival of the pulse at the first physical location from the arrival of the pulse at the second physical location, but close enough to provide sufficient assurance of arterial consistency. In some specific implementations, the distance ΔD between the first and the second arterial distension sensors 206 and 208 can be in the range of about 1 cm to about 30 cm, and in some implementations, less than or equal to about 20 cm, and in some implementations, less than or equal to about 10 cm, and in some specific implementations less than or equal to about 5 cm. In some other implementations, the distance ΔD between the first and the second arterial distension sensors 206 and 208 can be less than or equal to 1 cm, for example, about 0.1 cm, about 0.25 cm, about 0.5 cm or about 0.75 cm. By way of reference, a typical PWV can be about 15 meters per second (m/s). Using an ambulatory monitoring device in which the first and the second arterial distension sensors 206 and 208 are separated by a distance of about 5 cm, and assuming a PWV of about 15 m/s implies a PTT of approximately 3.3 milliseconds (ms).

The value of the magnitude of the distance ΔD between the first and the second arterial distension sensors 206 and 208, respectively, can be preprogrammed into a memory within a monitoring device that incorporates the sensors (for example, such as the memory 418 described below with reference to FIG. 4). As will be appreciated by a person of ordinary skill in the art, the spatial length L of a pulse can be greater than the distance ΔD from the first arterial distension sensor 206 to the second arterial distension sensor 208 in such implementations. As such, although the diagrammatic pulse 202 shown in FIG. 2 is shown as having a spatial length L comparable to the distance between the first arterial distension sensor 206 and the second arterial distension sensor 208, in actuality each pulse can typically have a spatial length L that is greater and even much greater than (for example, about an order of magnitude or more than) the distance ΔD between the first and the second arterial distension sensors 206 and 208.

Sensing Architecture and Topology

In some implementations of the ambulatory monitoring devices disclosed herein, both the first arterial distension sensor 206 and the second arterial distension sensor 208 are sensors of the same sensor type. In some such implementations, the first arterial distension sensor 206 and the second arterial distension sensor 208 are identical sensors. In such implementations, each of the first arterial distension sensor 206 and the second arterial distension sensor 208 utilizes the same sensor technology with the same sensitivity to the arterial distension signal caused by the propagating pulses, and has the same time delays and sampling characteristics. In some implementations, each of the first arterial distension sensor 206 and the second arterial distension sensor 208 is configured for ultrasound sensing. In some other implementations, each of the first arterial distension sensor 206 and the second arterial distension sensor 208 is configured for photoplethysmography (PPG) sensing, a type of optical sensing. In some other implementations, each of the first arterial distension sensor 206 and the second arterial distension sensor 208 is configured for impedance plethysmography (IPG) sensing, also referred to in biomedical contexts as bioimpedance sensing. In various implementations, whatever types of sensors are utilized, each of the first and the second arterial distension sensors 206 and 208 broadly functions to capture and provide arterial distension data indicative of an arterial distension signal resulting from the propagation of pulses through a portion of the artery proximate to which the respective sensor is positioned. For example, the arterial distension data can be provided from the sensor to a processor in the form of voltage signal generated or received by the sensor based on a light intensity or impedance signal sensed by the respective sensor.

As described above, during the systolic phase of the cardiac cycle, as a pulse propagates through a particular location along an artery, the arterial walls expand according to the pulse waveform and the elastic properties of the arterial walls. Along with the expansion is a corresponding increase in the volume of blood at the particular location or region, and with the increase in volume of blood an associated change in one or more characteristics in the region. Conversely, during the diastolic phase of the cardiac cycle, the blood pressure in the arteries decreases and the arterial walls contract. Along with the contraction is a corresponding decrease in the volume of blood at the particular location, and with the decrease in volume of blood an associated change in the one or more characteristics in the region.

In the context of bioimpedance sensing (or impedance plethysmography), the blood in the arteries has a greater electrical conductivity than that of the surrounding or adjacent skin, muscle, fat, tendons, ligaments, bone, lymph or other tissues. The susceptance (and thus the permittivity) of blood also is different from the susceptances (and permittivities) of the other types of surrounding or nearby tissues. As a pulse propagates through a particular location, the corresponding increase in the volume of blood results in an increase in the electrical conductivity at the particular location (and more generally an increase in the admittance, or equivalently a decrease in the impedance). Conversely, during the diastolic phase of the cardiac cycle, the corresponding decrease in the volume of blood results in an increase in the electrical resistivity at the particular location (and more generally an increase in the impedance, or equivalently a decrease in the admittance).

A bioimpedance sensor generally functions by applying an electrical excitation signal at an excitation carrier frequency to a region of interest via two or more input electrodes, and detecting an output signal (or output signals) via two or more output electrodes. In some more specific implementations, the electrical excitation signal is an electrical current signal injected into the region of interest via the input electrodes. In some such implementations, the output signal is a voltage signal representative of an electrical voltage response of the tissues in the region of interest to the applied excitation signal. The detected voltage response signal is influenced by the different, and in some instances time-varying, electrical properties of the various tissues through which the injected excitation current signal is passed. In some implementations in which the bioimpedance sensor is operable to monitor blood pressure, heartrate or other cardiovascular characteristics, the detected voltage response signal is amplitude- and phase-modulated by the time-varying impedance (or inversely the admittance) of the underlying arteries, which fluctuates synchronously with the user's heartbeat as described above. To determine various biological characteristics, information in the detected voltage response signal is generally demodulated from the excitation carrier frequency component using various analog or digital signal processing circuits, which can include both passive and active components.

In the context of optical sensing, and in particular photoplethysmography (PPG), the absorbance of light is greater by the blood in the arteries than that of the surrounding or adjacent skin, muscle, fat, tendons, ligaments, bone, lymph or other tissues. As similarly described above, as a pulse propagates through a particular location, the corresponding increase in the volume of blood results in an increase in the absorption of light at the particular location.

In some examples incorporating ultrasound sensors, measurements of arterial distension may involve directing ultrasonic waves into a limb towards an artery, for example, via one or more ultrasound transducers. Such ultrasound sensors also are configured to receive reflected waves that are based, at least in part, on the directed waves. The reflected waves may include scattered waves, specularly reflected waves, or both scattered waves and specularly reflected waves. The reflected waves provide information about the arterial walls, and thus the arterial distension.

In some implementations, regardless of the type of sensors utilized for the first arterial distension sensor 206 and the second arterial distension sensor 208, both the first arterial distension sensor 206 and the second arterial distension sensor 208 can be arranged, assembled or otherwise included within a single housing of a single ambulatory monitoring device. As described above, the housing and other components of the monitoring device can be configured such that when the monitoring device is affixed or otherwise physically coupled to a subject, both the first arterial distension sensor 206 and the second arterial distension sensor 208 are in contact with or in close proximity to the skin of the user at first and second locations, respectively, separated by a distance ΔD, and in some implementations, along a stretch of the artery between which various arterial properties can be assumed to be relatively constant. In various implementations, the housing of the ambulatory monitoring device is a wearable housing or is incorporated into or integrated with a wearable housing. In some specific implementations, the wearable housing includes (or is connected with) a physical coupling mechanism for removable non-invasive attachment to the user. The housing can be formed using any of a variety of suitable manufacturing processes, including injection molding and vacuum forming, among others. In addition, the housing can be made from any of a variety of suitable materials, including, but not limited to, plastic, metal, glass, rubber and ceramic, or combinations of these or other materials. In particular implementations, the housing and coupling mechanism enable full ambulatory use. In other words, some implementations of the wearable monitoring devices described herein are non-invasive, not physically-inhibiting and generally do not restrict the free uninhibited motion of a subject's arms or legs, enabling continuous or periodic monitoring of cardiovascular characteristics such as blood pressure even as the subject is mobile or otherwise engaged in a physical activity. As such, the ambulatory monitoring device facilitates and enables long-term wearing and monitoring (for example, over days, weeks or a month or more without interruption) of one or more biological characteristics of interest to obtain a better picture of such characteristics over extended durations of time, and generally, a better picture of the user's health.

Figure 3A:
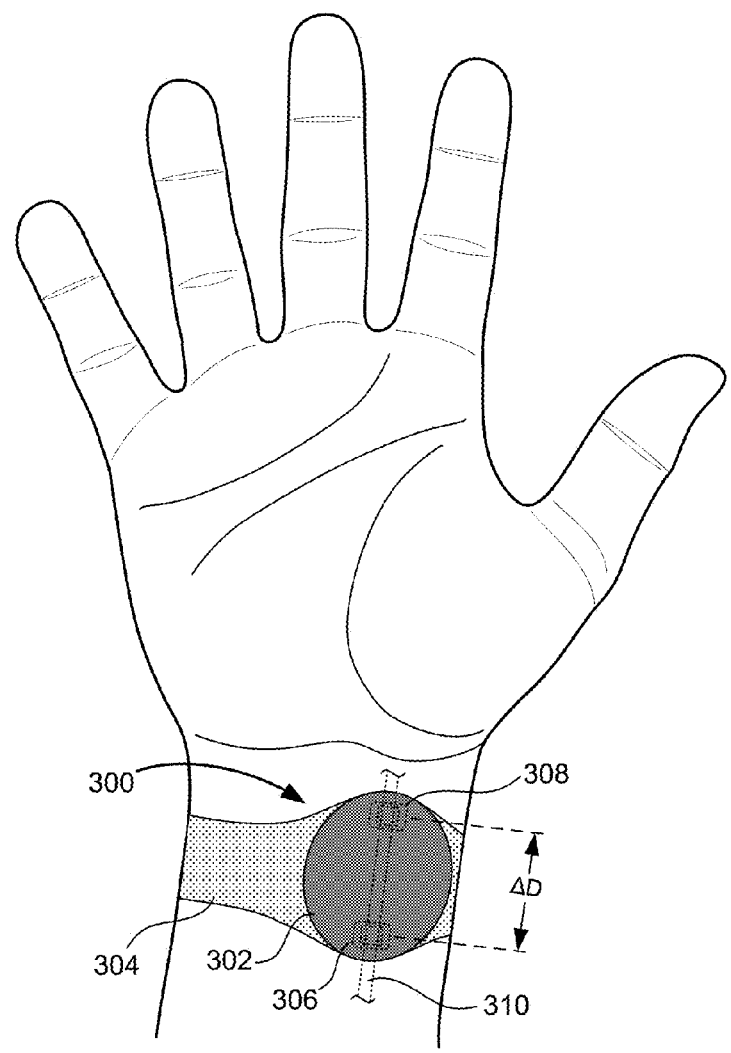
FIG. 3A shows an example ambulatory monitoring device designed to be worn around a wrist according to some implementations.
Figure 3B:
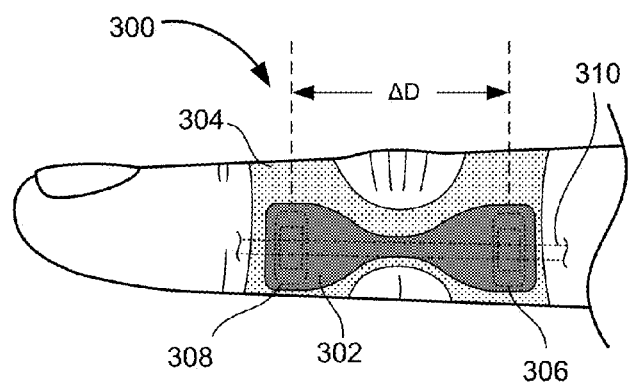
FIG. 3B shows an example ambulatory monitoring device designed to be worn around a finger according to some implementations.

In some implementations, the ambulatory monitoring device can be positioned around a wrist of a user with a strap or band, similar to a watch or fitness/activity tracker. FIG. 3A shows an example ambulatory monitoring device 300 designed to be worn around a wrist according to some implementations. In the illustrated example, the monitoring device 300 includes a housing 302 integrally formed with, coupled with or otherwise integrated with a wristband 304. The ambulatory monitoring device 300 is coupled around the wrist such that the first and the second arterial distension sensors 306 and 308 within the housing 302 are each positioned along a segment of the radial artery 310 (note that the sensors are generally hidden from view from the external or outer surface of the housing facing the subject while the monitoring device is coupled with the subject, but exposed on an inner surface of the housing to enable the sensors to obtain measurements through the subject's skin from the underlying artery). Also as shown, the first and the second arterial distension sensors 306 and 308 are separated by a fixed distance ΔD. In some other implementations, the ambulatory monitoring device 300 can similarly be designed or adapted for positioning around a forearm, an upper arm, an ankle, a lower leg, an upper leg, or a finger (all of which are hereinafter referred to as "limbs") using a strap or band. FIG. 3B shows an example ambulatory monitoring device 300 designed to be worn around a finger according to some implementations. In some other implementations, the ambulatory monitoring devices disclosed herein can be positioned on a region of interest of the user without the use of a strap or band. For example, the first and the second arterial distension sensors 306 and 308 and other components of the monitoring device can be enclosed in a housing that is secured to the skin of a region of interest of the user using an adhesive or other suitable attachment mechanism (an example of a "patch" monitoring device).

Figure 4:
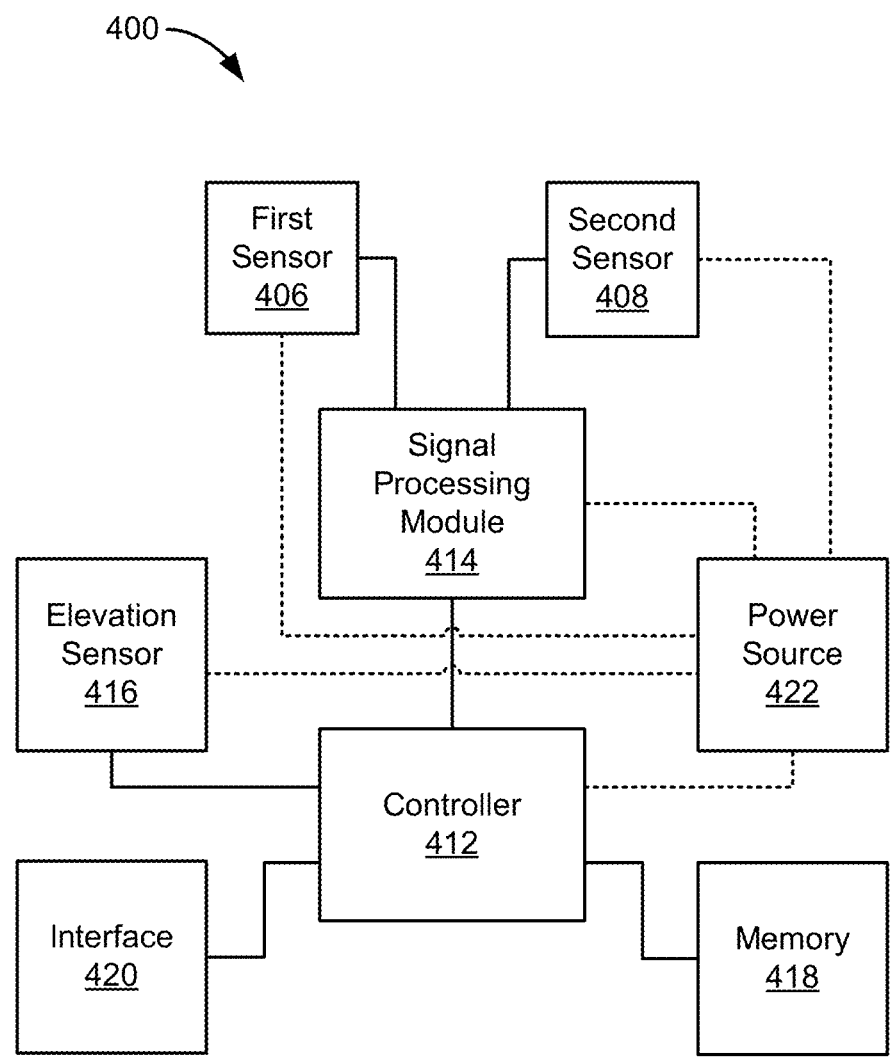
FIG. 4 shows a block diagram representation of components of an example ambulatory monitoring device according to some implementations.

FIG. 4 shows a block diagram representation of components of an example ambulatory monitoring device 400 according to some implementations. For example, the monitoring device 400 can be a block diagram representation of the monitoring device 300 shown in and described with reference to either of FIG. 3A or 3B above. As shown, the monitoring device 400 includes, in addition to the first arterial distension sensor 406 and the second arterial distension sensor 408, a controller 412 (also used interchangeably with and referred to herein as a "control unit," a "processor" or a "processing unit") electrically coupled with the first arterial distension sensor 406 and the second arterial distension sensor 408. While the controller 412 is shown and described as a single component, in some implementations, the controller 412 can collectively refer to two or more distinct control units or processing units in electrical or optical communication with one another. In some implementations, the controller 412 includes one or more of a general purpose single- or multi-chip processor, a central processing unit (CPU), a digital signal processor (DSP), a graphics processing unit (GPU), an application specific integrated circuit (ASIC), a field programmable gate array (FPGA) or other programmable logic device (PLD), discrete gate or transistor logic, discrete hardware components, or any combination thereof designed to perform the functions and operations described herein.

In the illustrated implementation, the raw arterial distension data (also referred to herein generally as "raw sensor data" or "sensor data") detected, measured, captured or sensed (hereinafter used interchangeably) by each of the first arterial distension sensor 406 and the second arterial distension sensor 408 can be sent, transmitted, communicated or otherwise provided to a signal processor 414. The signal processor 414 can include any suitable combination of hardware and software configured, adapted or otherwise operable to detect or extract an arterial distension signal (or other signals of interest) based on the raw arterial distension data received from the first arterial distension sensor 406 and the second arterial distension sensor 408. In some implementations, the signal processor 414 can include signal processing circuits or circuit components including, for example, amplifiers (such as instrumentation amplifiers), analog or digital mixers or multipliers, switches, analog-todigital converters (ADCs), passive or active analog filters, among others. In some implementations, one or more of such circuits or circuit components can be integrated within the controller 412, for example, where the controller 412 is implemented as a system-on-chip or system-in-package. In some implementations, one or more of such circuits or circuit components can be integrated within a DSP, GPU, CPU included within or coupled with the controller 412. In some implementations, the signal processor 414 can be implemented at least partially via software. For example, one or more functions of, or operations performed by, one or more of the circuits or circuit components just described can instead be performed by one or more software programs executing, for example, in a processor of the controller 412 (such as in a general purpose processor, CPU, GPU or DSP).

The monitoring device 400 also can include an elevation sensor 416 for determining an elevation (also used interchangeably with and referred to as a "height") of the device. In some implementations, the elevation can be a differential elevation relative to a previous elevation, a differential elevation relative to a reference elevation, or an absolute elevation (or altitude). In various implementations, the elevation sensor 416 can collectively refer to one or more of each of a plurality of different types of sensors. For example, the elevation sensor 416 can include one or more accelerometers or one or more gyroscopes for detecting relative motion and orientation. In some implementations, the position and elevation of the monitoring device 400 can be tracked using such sensors. Additionally or alternatively, the elevation sensor 416 can include an absolute elevation sensor such as a high resolution barometric altimeter. Additionally or alternatively, a magnetic near-field navigation system can be integrated in the monitoring device 400 to provide elevation estimates. Near-field magnetic devices can be advantageous in some implementations because the magnetic field is essentially unperturbed by biological objects, in contrast to electric near-field methods or schemes based on propagating radio waves. Additionally, the resolution of a near-field magnetic device is not hampered by effects of a non-zero wavelength, which is the case for devices based on propagating waves.

The controller 412 can store data in a memory 418. For example, the data can include raw arterial distension data obtained from the sensors 406 and 408, filtered or otherwise processed arterial distension data obtained based on the raw arterial distension data, or calculated or estimated data determined based on such raw or processed arterial distension data. The memory 418 also can include processor-executable code or other executable computer-readable instructions capable of execution by the controller 412 to perform various operations (or to cause other components such as the sensors or other modules to perform operations), including any of the calculations, estimations or other determinations described herein (including those presented in any of the equations below). The memory 418 can collectively refer to one or more memory devices (or "components"). In some implementations, one or more of the memory components can be implemented as a NOR- or NAND-based Flash memory array. In some other implementations, one or more of the memory components can be implemented as a different type of non-volatile memory. Additionally, in some implementations, one or more of the memory components can include a volatile memory array such as, for example, a type of RAM.

In some implementations, the controller 412 can communicate data stored in the memory 418 or data received directly from the signal processor 414 to an interface 420. The interface 420 also can collectively refer to one or more interfaces of one or more various types. In some implementations, the interface 420 can include a memory interface for receiving data from or storing data to an external memory such as a removable memory device. Additionally or alternatively, the interface 420 can include one or more wireless network interfaces or one or more wired network interfaces enabling the transfer of raw or processed data to, as well as the reception of data from, an external computing device, system, or server.

A power supply 422 can provide power to some or all of the components in the device 400. The power supply 422 can include one or more of a variety of energy storage devices. For example, the power supply 422 can include a rechargeable battery, such as a nickel-cadmium battery or a lithium-ion battery. Additionally or alternatively, the power supply 422 can include one or more supercapacitors. In some implementations, the power supply 422 can be chargeable (or "rechargeable") using power accessed from, for example, a wall socket (or "outlet") or a photovoltaic device or array. Additionally or alternatively, the power supply 422 can be wirelessly chargeable. The power supply 422 also can include a renewable energy source, such as a photovoltaic cell (also referred to as a "solar cell").

As described above, in some implementations, the housing and other components of the ambulatory monitoring device 400 are configured such that when the monitoring device is affixed to a subject, both the first arterial distension sensor 406 and the second arterial distension sensor 408 are in contact with or in close proximity to the skin of the user and separated from one another by a fixed (or fixable) distance $\Delta D$. For example, the housing can house, hold or otherwise maintain the position of the first arterial distension sensor 406 and the second arterial distension sensor 408 such that the distance $\Delta D$ between the sensors is fixed or constant. In some implementations, the distance $\Delta D$ of separation between the first arterial distension sensor 406 and the second arterial distension sensor 408 is in the range of about 1 cm to about 30 cm, and in some implementations, less than or equal to about 20 cm, and in some implementations, less than or equal to about 10 cm. In one specific implementation, the distance $\Delta D$ between the first and the second arterial distension sensors 406 and 408, respectively, is 5 cm. In some other implementations, the distance $\Delta D$ between the first and the second arterial distension sensors 406 and 408 can be less than or equal to 1 cm, for example, about 0.1 cm, about 0.25 cm, about 0.5 cm or about 0.75 cm. In some implementations, the locations of the first and the second arterial distension sensors 406 and 408, respectively, between which the PTT is determined, are locations between which the arterial properties can be assumed to be relatively or approximately constant. For example, the first and the second arterial distension sensors 406 and 408, respectively, can advantageously be positioned along a stretch of an artery over which there are negligible arterial discontinuities.

Arterial discontinuities, such as sharp bends, bifurcations, branches, forks or mergers of arteries, can cause reflections of propagating pulses. The reflections can be manifested in the form of counter-propagating pulse waves that can hinder the ascertainment of the proper temporal locations of pulses at the first and second locations where the first and the second arterial distension sensors 406 and 408, respectively, are positioned. Such hindrance can be exacerbated if the magnitudes of the reflected waves fluctuate. Such arterial discontinuities can be more prevalent in the distant peripheral regions of the arterial system, for example, such as in the hand and fingers. To reduce the likelihood of such arterial discontinuities, in some implementations, the monitoring device 400 is positioned around the wrist or forearm, for example, such that the first and the second arterial distension sensors 406 and 408, respectively, are each positioned along a segment of the radial or ulnar artery. In some other implementations, the monitoring device can be positioned around the upper arm, for example, such that the first and the second arterial distension sensors 406 and 408, respectively, are each positioned along a segment of the brachial artery. In some other implementations, the monitoring device can be positioned around a finger, for example, such that the first and the second arterial distension sensors 406 and 408, respectively, are each positioned along a segment of a digital artery.

Additionally or alternatively, in some implementations, the controller 412 can be configured to perform one or more reflection component removal and/or mitigation operations to better isolate the forward propagating components of the dominant pressure pulses of interest. For example, in some implementations, the controller 412 can be configured to record several (for example, 10) consecutive cardiac cycles' worth of arterial distension data. The arterial distension data obtained over the several cycles via the first and the second arterial distension sensors is then correlated by the controller 412 to average out any disturbances due to reflections. In some implementations, the portion of the arterial system in the subject's arm is assumed to have a common distribution of bifurcations and other arterial discontinuities to facilitate the separation of reflected waves from the portion of the arterial distension waveform associated with the systolic upstroke. For example, such wave separation techniques are well known in transmission line theory and waveguide propagation theory. Filtering techniques also can be used to mitigate the effects of reflections, for example, by enhancing higher frequency components of the systolic upstroke. The use of reflection component removal and/or mitigation operations can enable accurate measurements even if the monitoring device 400 is positioned along a segment of an artery that includes arterial discontinuities or other irregularities.

In various implementations, the controller 412 is capable of (also used interchangeably with and referred to herein as "configured to," "operable to," "adapted to," "manufactured to," and "programmed to") identifying, registering or otherwise determining the arrival or presence of a pulse at each of the first and the second physical locations based on the arterial distension data received from the first and the second arterial distension sensors 406 and 408, respectively. In some implementations, the controller 412 is configured to register a pulse based on a detected onset of the pulse as determined from the arterial distension data. In other words, for example, when the arterial distension data obtained from the first arterial distension sensor 406 indicates an onset of a pulse, the controller 412 registers the associated time as the first temporal location. Similarly, when the arterial distension data obtained from the second arterial distension sensor 408 indicates an onset of the pulse, the controller 412 registers the associated time as the second temporal location. In some other implementations, it can be desirable to register, as the time associated with the pulse, the time at which the arterial distension data indicates that the gradient is the steepest. For example, it is generally true that the best temporal localization of any signal (a pulse wave in the present context) is associated with the time at which the gradient is steepest.

The time at which the gradient is the steepest is generally not at the onset of the pulse, but instead, typically at some time during the systolic upstroke prior to the peaking at the systolic pressure. In some such implementations, for example, when the arterial distension data obtained from the first arterial distension sensor 406 indicates that the magnitude of the gradient has reached a local maximum (that is, when the gradient is the steepest during a given cardiac cycle), the controller 412 registers the associated time as the first temporal location. Similarly, when the arterial distension data obtained from the second arterial distension sensor 408 indicates that the magnitude of the gradient has reached a local maximum, the controller 412 registers the associated time as the second temporal location. In some other implementations, when the arterial distension data obtained from the first arterial distension sensor 406 indicates that the magnitude of the gradient has crossed a threshold (for example, reached or exceeded a threshold value pre-programmed into the memory 418 or statically or dynamically determined by the controller 412), the controller 412 registers the associated time as the first temporal location. Similarly, when the arterial distension data obtained from the second arterial distension sensor 408 indicates that the magnitude of the gradient has crossed (for example, reached or exceeded a threshold value), the controller 412 registers the associated time as the second temporal location.

Figure 5:
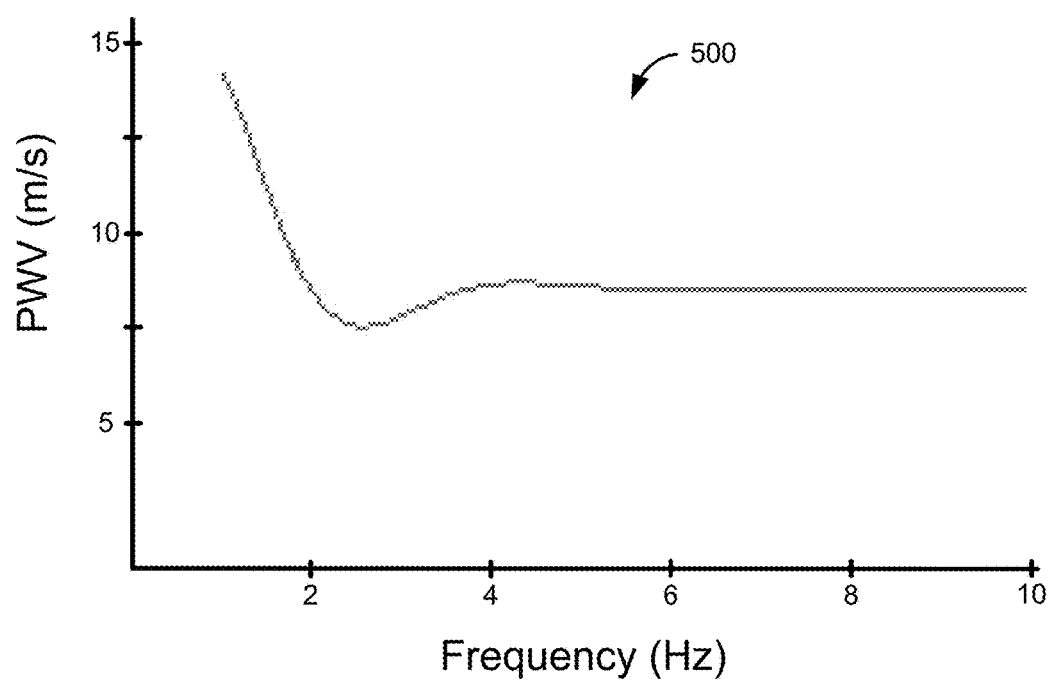
FIG. 5 shows a plot of an example calculated pulse wave velocity (PWV) curve for an example pulse as a function of frequency.

In some implementations, the raw arterial distension data obtained by the first and the second arterial distension sensors 406 and 408 is advantageously processed using high-pass filtering techniques. In some such implementations, the signal processor 414 performs one or more high-pass filtering operations on the raw arterial distension data using, for example, one or more analog or digital filtering operations performed via any suitable combination of software and hardware including digital or discrete components, and in some instances, one or more passive or active filter components. Such high-pass filtering can advantageously be used to significantly reduce low spectral frequency components, for example, having frequencies below a few Hertz (Hz) (for example, below 3 Hz or below 4 Hz). Such low spectral frequency components can be caused by motion artifacts, respiration artifacts or from low frequency propagating waves not of interest. These low spectral frequency components may propagate with velocities different than the velocity of higher spectral components of interest. This phenomenon reflects a nonlinear dispersion relation for pulse propagation. FIG. 5 shows a plot of an example calculated pulse wave velocity (PWV) curve 500 for an example pulse as a function of frequency. Notably, the PWV curve 500 is approximately constant for higher frequency components above, for example, 3 or 4 Hz. It has been observed that the velocities of the higher spectral components may provide the best representation of PWV.

It should also be appreciated that the raw arterial distension data obtained by the first and the second arterial distension sensors 406 and 408 also can advantageously be processed using low-pass filtering techniques or bandpass filtering techniques. In some such implementations, the signal processor 414 performs one or more low-pass filtering operations on the raw arterial distension data using, for example, one or more analog or digital filtering operations performed via any suitable combination of software and hardware including digital or discrete components, and in some instances, one or more passive or active filter components. Such low-pass filtering can advantageously be used to significantly reduce high frequency noise components outside of the frequency band of interest.

Stress-Strain Relationship

Figure 6:
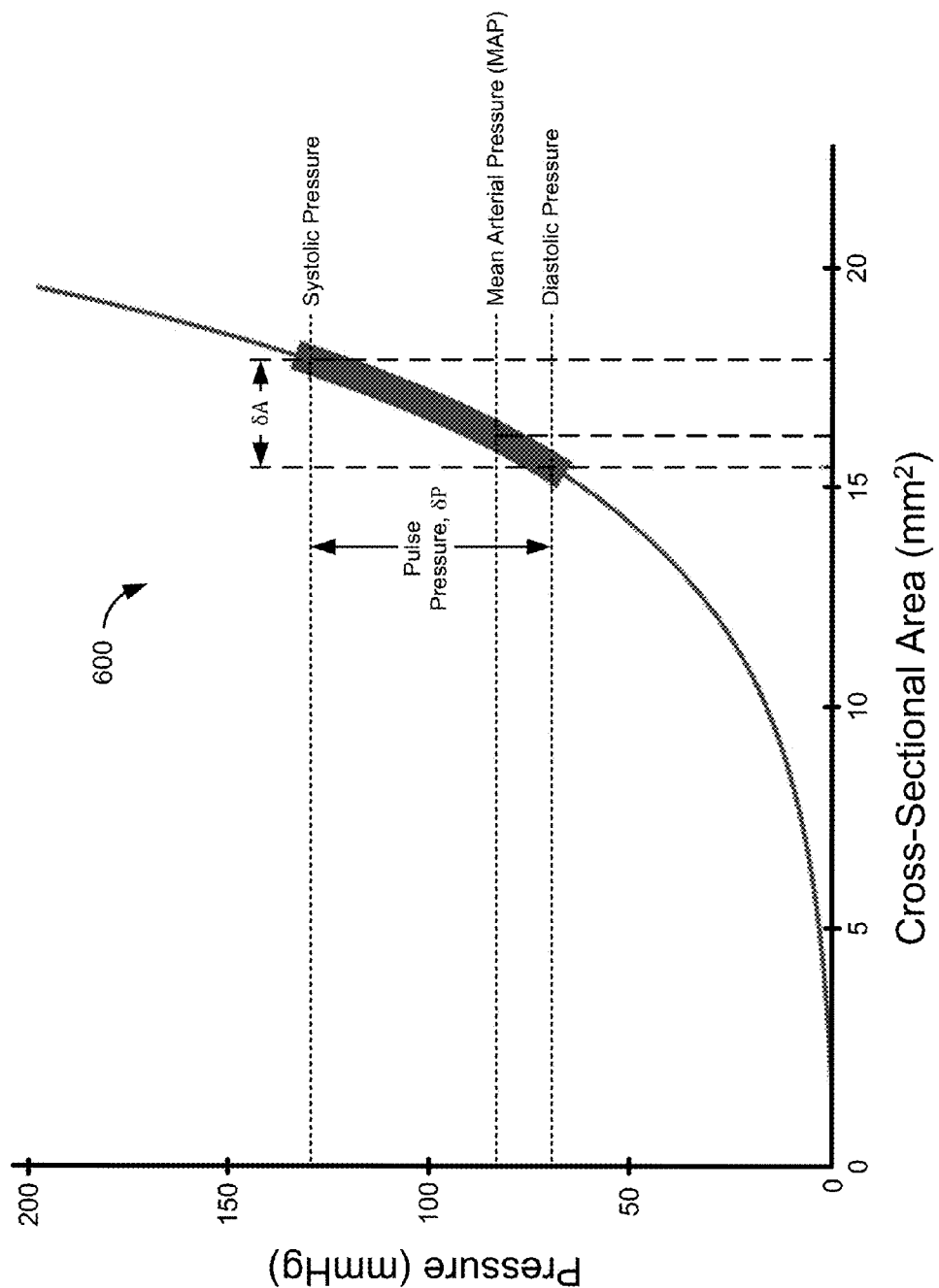
FIG. 6 shows a plot of an example calculated blood pressure curve as a function of cross-sectional area during a cardiac cycle.

In some implementations, to determine an estimate of the transmural blood pressure based on a measurement of the PWV, a relationship between the transmural blood pressure and the PWV is used. In some such implementations, to provide the relationship between the transmural blood pressure and PWV, a stress-strain relationship is used to express the elastic properties of the arterial wall in the form of a relationship between the transmural blood pressure P and the cross-sectional area A of the artery. FIG. 6 shows a plot of an example calculated blood pressure curve 600 as a function of cross-sectional area during a cardiac cycle. In some implementations, the stress-strain relationship is modeled as an exponential relationship, for example, in the form of equation 1 below.

$$P = P_0(e^{A/A_0} - 1) \quad (1)$$

In equation 1, P is the transmural blood pressure at a particular location along an artery at a particular time, A is the cross-sectional area of the artery at the location and time, and $P_0$ and $A_0$ are parameters characterizing the relationship. The parameters $P_0$ and $A_0$ (hereinafter also referred to as "stress-strain parameters") can be considered to be constant over short time durations (for example, seconds or minutes), but can change over time if the smooth muscles surrounding the artery contract (tighten) or dilate (relax) (in other words, the elastic properties of the artery vary as a function of arterial smooth muscle contraction or dilation). The exponential relationship represented in equation 1 provides desirable results for realistic blood pressures, which are generally in the range of about 35 millimeters of mercury (mmHg) to 250 mmHg.

The stress-strain relationship shown as equation 1 can be inverted to express the cross-sectional area A as a function of the pressure P, yielding equation 2 below:

$$A = A_0 \ln\left[\frac{P + P_0}{P_0}\right], \quad (2)$$

where "ln" denotes the natural logarithm. In some implementations, the PWV can be related to pressure variation by the Bramwell-Hill equation shown below as equation 3.

$$PWV = \sqrt{\frac{\partial P}{\partial V} \frac{V}{\rho}} \quad (3)$$

In equation 3, V represents the arterial lumen (blood volume) and ρ represents the blood density. In some implementations, the volume V is substituted with the cross-sectional area A because the expansion of the artery in the direction of the blood flow with increasing pressure P can be neglected. This leads to the following approximation shown as equation 4.

$$PWV \cong \sqrt{\frac{\partial P}{\partial A} \frac{A}{\rho}} \quad (4)$$

Additionally, in some implementations, the derivative of the pressure P with respect to the cross-sectional area A is approximated by a ratio of incremental values, for example, by the pulse pressure over the distension of the artery. This leads to the following approximation shown as equation 5.

$$PWV \cong \sqrt{\frac{\delta P}{\delta A} \frac{A}{\rho}} \quad (5)$$

By combining equations 2 and 5, PWV can be expressed as a function of transmural blood pressure P as shown in equation 6 below.

$$PWV(P \mid P_0) = \sqrt{\frac{(P_0 + P) \ln \frac{(P_0 + P)}{P_0}}{\rho}} \quad (6)$$

Figure 7:
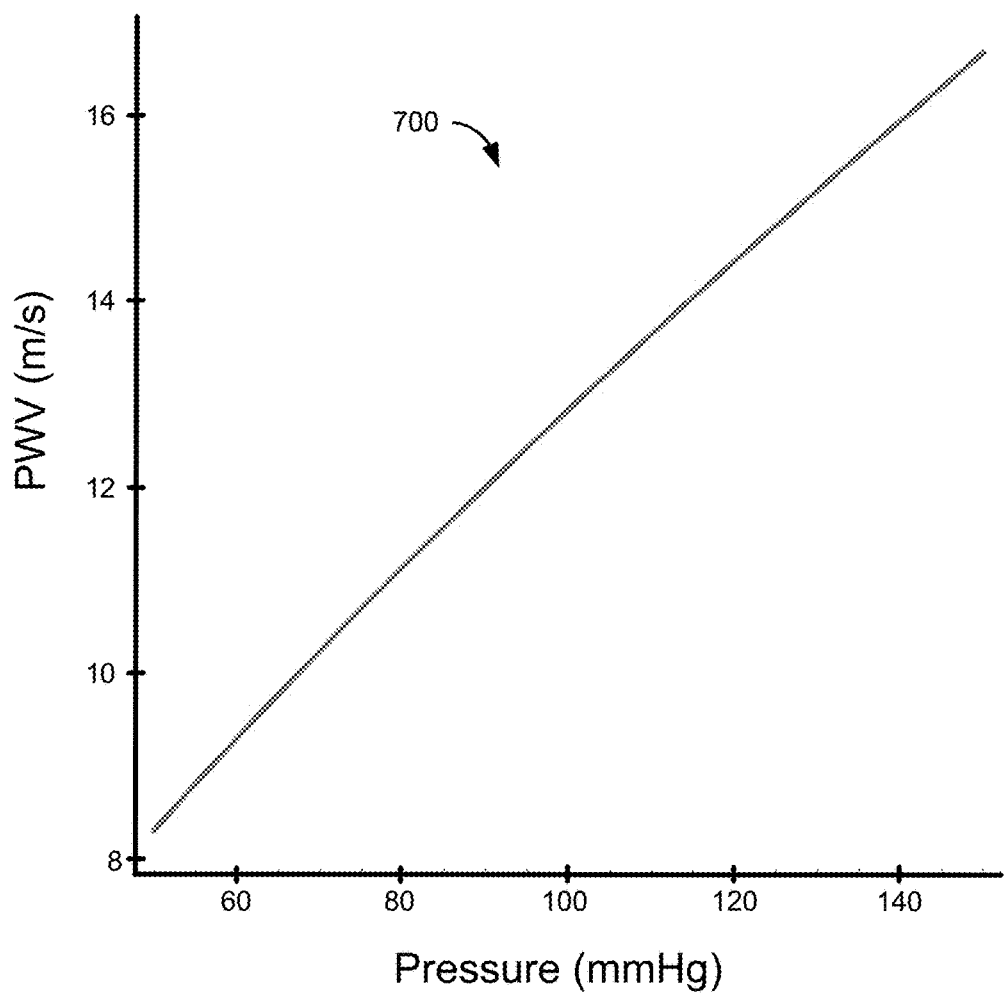
FIG. 7 shows a plot of an example calculated pulse wave velocity (PWV) curve as a function of mean transmural blood pressure.

Again, equation 6 expresses PWV as a function of the transmural blood pressure P, which, as described above, is interpreted as the mean transmural pressure (averaged over a pulse) and conditioned by the stress-strain parameter $P_0$. The mean transmural blood pressure P can thus be expressed as a function of PWV by solving equation 6 for P. In some implementations, a numerical solution is used to solve for the mean transmural blood pressure P based on PWV data. FIG. 7 shows a plot of an example calculated pulse wave velocity (PWV) curve 700 as a function of mean transmural blood pressure. In some implementations, such a numerical solution can be previously ascertained and the results can be programmed into the memory 418 (not all values need be programmed because the controller 412 can be configured to perform interpolation). In some other implementations, the controller 412 can determine numerical or analytical solutions to various equations described herein.

Generally, at least two parameters have been necessary to characterize any relevant stress-strain relationship for an artery. In traditional approaches, at least one of the parameters is estimated by calibration with an external reference device or estimated empirically on the basis of person-specific attributes such as age and gender, which may not provide the necessary additional information about the stress-strain relationship needed for accuracy or reliability. In contrast, various implementations relate to estimating blood pressure P based on PWV without the use of or need for calibration by an external reference device and without the use of previously known or inferred person-specific attributes. In various implementations, the relationship or model represented by equation 6 enables the estimation of the transmural blood pressure P based on PWV without the use of or need for calibration by an external reference device or person-specific attributes because only one of the unknown parameters (for example, $P_0$) is needed. In other words, equation 6 enables the determination of the blood pressure based on a relationship or model between blood pressure and PWV that includes the stress-strain parameter $P_0$ and no other stress-strain parameters.

The efficacy of the relationship represented by equation 6 can be demonstrated as follows. First, it is generally true that all plausible stress-strain relationships will show a positive gradient in regions of the artery not under the influence of a pulse wave. Additionally, a general local representation of the stress-strain relationship can be obtained from a truncated Taylor series expansion evaluated around the expected mean arterial pressure. Performing such an expansion reveals that only one parameter of the stress-strain relationship needs to appear in an expression for PWV. Again, this realization is evidenced in the relationship represented by equation 6, which includes only one parameter ($P_0$) of the two parameters ($P_0$ and $A_0$) characterizing the stress-strain relationship represented by equation 1. This is a significant contrast compared with traditional approaches that define PWV versus pressure relationships that require at least two parameters (for example, $P_0$ and $A_0$). Also of significance, because only one parameter of the stress-strain relationship needs to appear in an expression for PWV in implementations described herein, calibration can be performed by, for example, the use of hydrostatic pressure measurements, which do not require any external reference device or the knowledge or inference of person-specific attributes.

Example Method for Estimating BP Based on PWV

Figure 8:
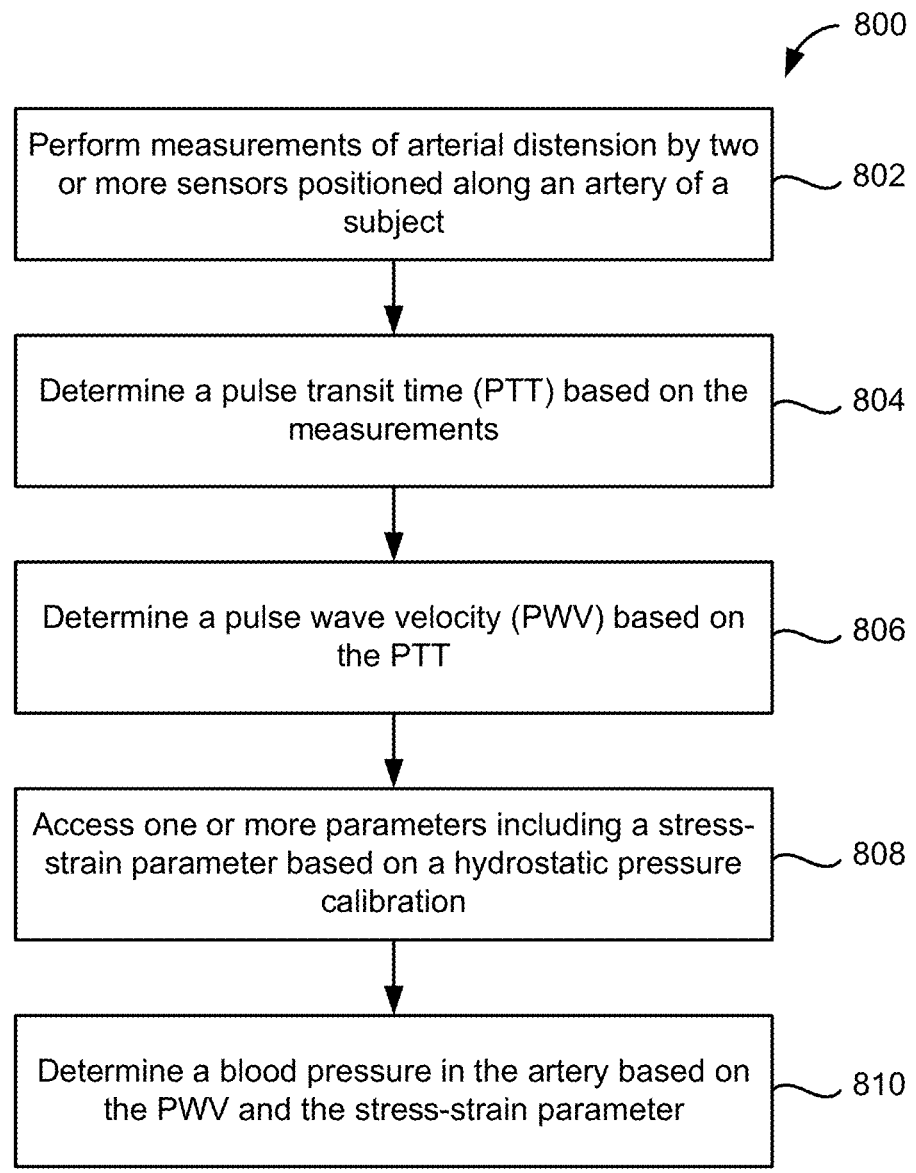
FIG. 8 shows a flow diagram showing an example process for estimating blood pressure based on pulse wave velocity (PWV) according to some implementations.

After $P_0$ is known, estimated, calculated or otherwise determined, the arterial pressure P at any elevation relative to the heart at which PWV is measured can be determined based on equation 6. FIG. 8 shows a flow diagram showing an example process 800 for estimating blood pressure based on pulse wave velocity (PWV) according to some implementations. In some implementations, the process 800 makes use of the relationship expressed in equation 6. In various implementations, the controller 412 can perform (or cause the performance of) process 800 continuously. For example, the controller 412 can cause the performance of process 800 periodically, such as every 2, 3, 4, 5, 10 or more seconds, every minute, every few minutes, every hour or every few hours, or at other suitable or desirable intervals.

In some implementations, the process 800 begins after the controller 412 prepares the monitoring device 400 (for example, including at least the first and the second arterial distension sensors 406 and 408) to perform measurements and to obtain sensor data based on the measurements. For example, the controller 412 prepares the first and the second arterial distension sensors 406 and 408, respectively, to perform measurements of the arterial distension of the artery of interest and to obtain arterial distension data based on the measurements. In some implementations, the controller 412 also prepares the elevation sensor 416 to obtain elevation data associated with the elevation of the monitoring device 400 (for example, an absolute elevation or an elevation relative to a reference elevation such as the heart level). The initial preparation can include, for example, retrieving and loading various control parameters from memory (for example, from memory 418), such as a value of the arterial stress-strain parameter $P_0$. Other values that can be retrieved and loaded from the memory 418 include, for example, a value of the blood density p as well as values of parameters specific to the type of sensors utilized for the first and the second arterial distension sensors 406 and 408. For example, if the first and the second arterial distension sensors 406 and 408 are ultrasound sensors, the preparation can include retrieving or otherwise selecting or determining values of an excitation frequency and amplitude of the ultrasonic pressure wave that will be generated when performing measurements of the arterial distension. Similarly, if the first and the second arterial distension sensors 406 and 408 are PPG sensors, the preparation can include retrieving or otherwise selecting or determining values of an excitation frequency and amplitude (intensity) of the incident light that will be generated when performing measurements of the arterial distension. Similarly, if the first and the second arterial distension sensors 406 and 408 are bioimpedance sensors, the preparation can include retrieving or otherwise selecting or determining values of an excitation carrier frequency and amplitude of the incident electrical current that will be generated when performing measurements of the arterial distension. In some implementations, the preparation also can include retrieving the value of the distance of separation ΔD between the first and the second arterial distension sensors 406 and 408.

In some implementations, the process 800 begins in block 802 with performing measurements of arterial distension by two or more sensors positioned along an artery of the subject. For example, the controller 412 can cause the first and the second arterial distension sensors 406 and 408, respectively, to obtain the measurements of the arterial distension data. The controller 412 also receives the arterial distension data from the first and the second arterial distension sensors 406 and 408 in block 802. For example, the controller 412 can receive the arterial distension data directly from the first and the second arterial distension sensors 406 and 408. In some other implementations, the signal processor 414 first receives the arterial distension data and subsequently passes the arterial distension data (or processed arterial distension data) to the controller 412 in block 802. In some implementations, the controller 412 also determines an arterial distension waveform in block 802 based on the arterial distension data.

The process 800 proceeds in block 804 with determining a PTT based on the measurements performed in block 802. For example, the controller 412 can detect a pulse at the first physical location based on the arterial distension data obtained by the first arterial distension sensor 406. As described above, the controller 412 can be configured to register a pulse at the first physical location based on a detected onset of the pulse as determined from the arterial distension data. In other words, for example, when the arterial distension data obtained from the first arterial distension sensor 406 indicates an onset of a pulse, the controller 412 registers the associated time as a first temporal location. As is also described above, in some other implementations, it can be desirable to register, as the time associated with the pulse, the time at which the arterial distension data indicates that the gradient is the steepest. The time at which the gradient is the steepest is generally not at the onset of the pulse, but rather, typically at some time during the systolic upstroke prior to the peaking at the systolic pressure. In some such implementations, for example, when the arterial distension data obtained from the first arterial distension sensor 406 indicates that the magnitude of the gradient has reached a local maximum (that is, when the gradient is the steepest during a given cardiac cycle), the controller 412 registers the associated time as the first temporal location. In some other such implementations, when the arterial distension data obtained from the first arterial distension sensor 406 indicates that the magnitude of the gradient has crossed a threshold (for example, reached or exceeded a threshold value pre-programmed into the memory 418 or statically or dynamically determined by the controller 412), the controller 412 registers the associated time as the first temporal location.

The determining of the PTT in block 804 also includes detecting, by the controller 412, the pulse at the second physical location based on the arterial distension data obtained by the second arterial distension sensor 408. As described above, the controller 412 can be configured to register a pulse at the second physical location based on a detected onset of the pulse as determined from the arterial distension data. In other words, for example, when the arterial distension data obtained from the second arterial distension sensor 408 indicates an onset of the pulse, the controller 412 registers the associated time as a second temporal location. As is also described above, in some other implementations, it can be desirable to register, as the time associated with the pulse, the time at which the arterial distension data indicates that the gradient is the steepest. In some such implementations, for example, when the arterial distension data obtained from the second arterial distension sensor 408 indicates that the magnitude of the gradient has reached a local maximum during the given cardiac cycle or has crossed a threshold, the controller 412 registers the associated time as the second temporal location.

The determining of the PTT in block 804 also includes determining, by the controller 412, the PTT based on the temporal distance between the first and the second temporal locations. As described above, determining the PTT can include calculating the time difference between the time associated with the first temporal location and the time associated with the second temporal location. In some implementations, the process then proceeds in block 806 with the controller 412 determining a pulse wave velocity (PWV) based on the determined PTT and the value of the known spatial distance ΔD between the first and the second arterial distension sensors 406 and 408. For example, the controller 412 can calculate the PWV as the quotient of the spatial distance ΔD divided by the PTT.

In some implementations, the process 800 proceeds in block 808 with the controller 412 accessing the stress-strain parameter $P_0$. In implementations in which the value of the arterial stress-strain parameter $P_0$ was earlier retrieved from the memory 418, accessing the arterial stress-strain parameter $P_0$ can simply include accessing the value of the arterial stress-strain parameter $P_0$ from a random access memory (RAM) included within or connected with the controller 412. In some implementations, the process 800 then proceeds in block 810 with the controller 412 determining an estimate of the blood pressure P in the artery of the subject based on the PWV and the value of the stress-strain parameter $P_0$. For example, the controller 412 can calculate or otherwise determine the blood pressure P of the subject based on the PWV and $P_0$ based on the relationship expressed in Equation 6. As described above, the mean transmural blood pressure P can be expressed as a function of PWV using equation 6. In some implementations, the controller 412 can be configured to use an analytical or numerical solution to solve for the mean transmural blood pressure P based on the PWV determined in block 806. In some other implementations, a numerical solution can be previously ascertained by another processing system such as an external computing system. In such latter implementations, the results of the numerical solution can then be programmed into the memory 418, for example, as a lookup table, at the end of the manufacturing process. In some such implementations, not all values of PWV and blood pressure P need be programmed because the controller 412 can be configured to perform interpolation between values.

In some implementations, the controller 412 also causes the elevation sensor 416 to obtain elevation data in block 802 concurrently, periodically, intermittently or in parallel with the obtainment of the arterial distension data. As described above, the elevation of the monitoring device 400 can be determined as an absolute elevation or as a relative elevation (for example, relative to a heart level reference or relative to a previous elevation). In such implementations, if the controller 412 determines that the elevation at which the arterial distension data used to determine the PWV is not at the heart level, the controller 412 can apply a correction for the difference in hydrostatic pressure at the elevation at which the arterial distension data is measured relative to the heart level.

Preprocessing and Filtering

Some implementations of the process 800 (and in some implementations, also the process 1000 described below) further include one or more preprocessing operations such as, for example, one or more high-pass filtering operations, one or more nonlinear filtering operations, one or more temporal localization operations, or one or more other signal processing operations. In various implementations, any of a number of suitable or desirable high-pass filtering, nonlinear filtering, temporal localization or other signal processing operations can be performed in any one of blocks 802, 804 or 806. Some of such operations can be performed by the signal processor 414, by the controller 412, or both. In some implementations, the signal processor 414 can perform the filtering (including both linear and nonlinear filtering) and other preprocessing operations on the raw arterial distension signals and subsequently communicate the filtered and otherwise processed arterial distension signals to the controller 412 for additional processing or for pulse detection. In some implementations, some signal processing operations can be performed by the signal processor 414 and some other signal processing operations can be performed by the controller 412.

High-pass filtering of the arterial distension data ("measurements") collected by the arterial distension sensors of the monitoring device is generally desirable because it enhances those parts of each pulse that exhibit the steepest temporal gradient, and thus, facilitates pulse detection. High-pass filtering also can be desirable because it can reduce or eliminate effects of a nonlinear dispersion relation, such as that shown and described with reference to FIG. 5. However, noise may limit the extent to which high-pass filtering is feasible.

Nonlinear filtering can be desirable in order to enhance the large amplitude parts of the pulse, and especially parts with large temporal gradients, which may occur during relatively short time periods. Again, such nonlinear filtering can facilitate pulse detection. In some implementations, one or more of the nonlinear filtering operations can include applying a function with a steadily increasing gradient to the arterial distension signals obtained by each of the first and the second arterial distension sensors 406 and 408. For example, if we denote one of the raw arterial distension signals as r(t), then for subsequent processing by the controller 412, the raw arterial distension signal r(t) is substituted with f(r(t)), where f(x) is a function with a gradient f'(x) that increases with increasing x. Such a function may be a higher order polynomial, an exponential function or any other suitable function known in the art.

Figure 9A:
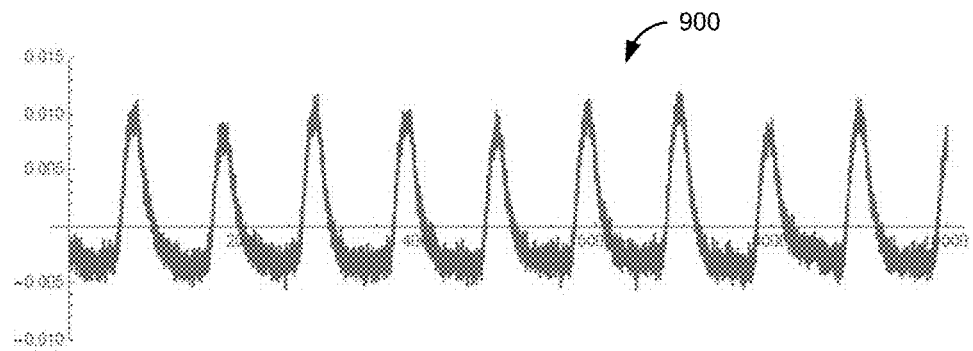
FIG. 9A shows a plot of the amplitude of an example raw arterial distension signal versus time.
Figure 9B:
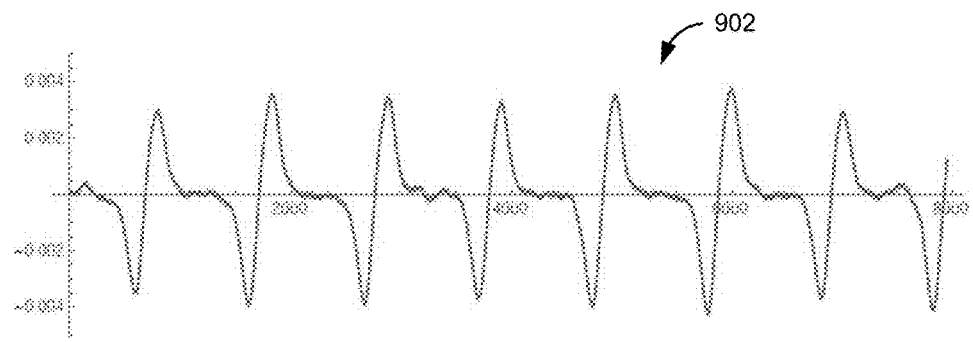
FIG. 9B shows a plot of the amplitude of an example filtered arterial distension signal obtained after filtering the raw arterial distension signal shown in FIG. 9A.

Examples of the filtering and other preprocessing operations (also referred to generally as "signal processing operations" or simply "processing operations") that can be performed on an arterial distension signal are shown and described with reference to FIGS. 9A-9C. FIG. 9A shows a plot of the amplitude of an example raw arterial distension signal 900 versus time. In the particular example shown, the raw arterial distension signal 900 was obtained using a PPG-based arterial distension sensor positioned along the radial artery at the subject's wrist. The sampling rate was 1 kHz. FIG. 9B shows a plot of the amplitude of an example filtered arterial distension signal 902 obtained after filtering the raw arterial distension signal shown in FIG. 9A. For example, the filtered version of the signal 902 can be obtained after filtering the raw arterial distension signal 900 of FIG. 9A with both a low-pass filter and a high-pass filter, both of which are of the FIR (Finite Impulse Response) type. The phase, and thus the delay, of such filters are very well defined so that they do not introduce delay errors. More specifically, the filtered version of the signal 902 shown in FIG. 9B was obtained after performing a low-pass filtering operation using a linear low-pass filter, and in particular, a Hann window truncation, having a low-pass cutoff frequency of 40 Hz. The low-pass-filtered signal was then subjected to a high-pass filtering operation using a linear high-pass filter, and in particular, an asymmetric Hann window truncation, having a high-pass cutoff frequency of 3 Hz, in order to accommodate the expected asymmetric pulse shape.

Figure 9C:
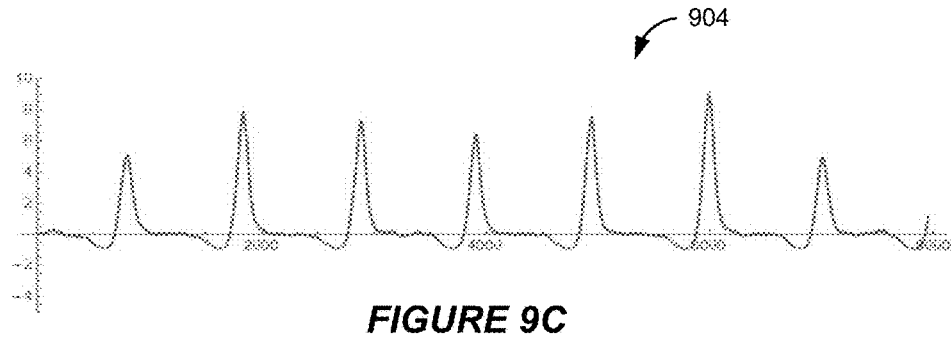
FIG. 9C shows a plot of the amplitude of an example nonlinearly-processed arterial distension signal obtained after nonlinearly processing the filtered signal shown in FIG. 9B.

FIG. 9C shows a plot of the amplitude of an example nonlinearly-processed arterial distension signal 904 obtained after nonlinearly processing the filtered signal 902 shown in FIG. 9B. In particular, FIG. 9C shows the result of applying an exponential function to the filtered arterial distension signal 902 of FIG. 9B. Expression 7 shows an example exponential function applied to the arterial distension signal 902 to produce the nonlinearly-processed arterial distension signal 904 of FIG. 9C.

$$\exp\left(\frac{r(t)}{\frac{1}{\Delta T}\int_t^{t+\Delta T}\sqrt{r(t)^2}\,dt}\right) \quad (7)$$

In equation 7, $\Delta T$ extends over six pulses. However, in other implementations a shorter or longer sliding average may be applied (for example, such as a sequence of pulses having a collective combined duration in the range of about 3 seconds to about 60 seconds or longer.

Parameter Determination Based on Hydrostatic Pressure Calibration

The hydrostatic pressure affects the transmural blood pressure P in a well-defined way, for example, because the circulatory system can be considered as a closed system. Generally, the hydrostatic pressure $P_H$ of any fluid can be expressed using equation 8 below.

$$P_H = h * \rho * g \quad (8)$$

In equation 8, g is the gravitational acceleration, $\rho$ is the density of the fluid, and h is the height (or elevation). If measurements are performed at two different elevations, and assuming that there are no other appreciable changes in the cardiovascular system, then the difference $\Delta P$ between the transmural blood pressures at the two elevations is given by equation 9 below:

$$\Delta P = \Delta h * \rho * g, \quad (9)$$

where $\Delta h$ is the elevation difference between the two elevations. The density $\rho$ of whole blood is approximately 1025 kg/m$^3$. The gravitational acceleration g is approximately 9.806 m/s$^2$ at sea level (the variation of the gravitational acceleration g with latitudinal and longitudinal location on the surface of the earth is negligible). Substituting these values into equation 9, an elevation difference $\Delta h$ of, for example, one meter (1 m) results in a pressure difference $\Delta P$ of approximately 75 mmHg, which is significant in relation to a typical mean arterial pressure of about 100 mmHg. As such, calibration based on hydrostatic pressure provides a reliable means of calibration without the need for a reference device or person-specific attributes. In some implementations, a hydrostatic pressure calibration is more specifically used to identify the unknown stress-strain parameter $P_0$ required for evaluating equation 6 for a given estimate of PWV.

To facilitate the identification of a general relationship for the unknown stress-strain parameter $P_0$ based on PWV estimates for each of a first elevation (for example, below the heart level) and a second elevation (for example, above the heart level), let c denote the product of the blood density $\rho$ and the square of the PWV value at an arbitrary elevation. Using this notation, equation 6 can be rewritten as equation 10 below.

$$c = \left[(P_0 + P)\ln\frac{(P_0 + P)}{P_0}\right] \quad (10)$$

Now define the first elevation to be at $\Delta h$ below a reference level h, and define the second elevation to be at $\Delta h$ above the reference level h. Additionally, let $c_-$ denote the product of the blood density $\rho$ and the square of the PWV value at the first elevation, let $c_+$ denote the product of the blood density $\rho$ and the square of the PWV value at the second elevation, and let $\Delta c$ denote the difference $c_+ - c_-$.

To simplify a general solution for $\Delta c$, a first Taylor series expansion of equation 10 can be performed around $P = P_{h+\Delta h}$ and a second Taylor series expansion equation 10 can be performed around $P = P_{h-\Delta h}$. Assuming that the height difference $\Delta h$ is relatively small, for example, less than or equal to about 30 cm, only the first two terms of each of the Taylor series expansions can provide sufficient accuracy. Equation 11 below shows the resultant approximation for $\Delta c$ based on the Taylor series expansions around $P = P_{h+\Delta h}$ and around $P = P_{h-\Delta h}$ using only the first two terms of each of the expansions.

$$\Delta P\left(1 + \ln\left[\frac{P_0 + P_h}{P_0}\right]\right) \cong \Delta c \equiv c_+ - c_- \quad (11)$$

In equation 11, $\Delta P$ represents the hydrostatic pressure difference between the second and first elevations; that is, $\Delta P = P_{h+\Delta h} - P_{h-\Delta h}$. Equation 11 can then be rearranged to yield equation 12 below.

$$\frac{P_0 + P_h}{P_0} = e^{\left(\frac{\Delta c}{\Delta P} - 1\right)} \quad (12)$$

Denoting $c_h$ as the product of the blood density $\rho$ and the square of the PWV at the reference level h, and referring back to equation 10, the value of $c_h$ can be expressed as equation 13 below.

$$c_h = (P_0 + P_h)\ln\left(\frac{P_0 + P_h}{P_0}\right) \quad (13)$$

Substituting equation 12 into equation 13 and rearranging yields an expression for the value of the stress-strain parameter $P_0$ as shown in equation 14 below. However, it should be noted that other implementations can use different approximations and derivation techniques to arrive at an equation for the stress-strain parameter $P_0$, and as such, equation 14 is not to be construed as limiting all implementations.

$$P_0 = \frac{c_h}{\frac{\Delta c}{\Delta p} - 1} - P_h \quad (14)$$

Notably, $\Delta P$, $\Delta c$, $P_h$ and $c_h$ all can be obtained from measurements during an initial hydrostatic pressure calibration in the implementations described herein. More specifically, and as described above, some implementations of the calibration require the subject wearing the monitoring device (for example, the monitoring device 300 or 400 described above) to position the device at two (or more) different elevations (for example, by rotating, lifting, lowering or otherwise positioning a limb onto which the device is mounted). In some implementations, the length of the duration of time during which the monitoring device is held at each of at least a first elevation and a second elevation spans at least one pulse, and in some cases, spans a sequence of pulses (for example, 2, 3, 5, 10 or more seconds). While being held at each of the first and the second elevations, at least a first arterial distension sensor (for example, first arterial distension sensor 306 or 406) and a second arterial distension sensor (for example, second arterial distension sensor 308 or 408) perform measurements of the arterial distension signal to obtain at least a first PTT estimate at the first elevation and a least a second PTT estimate at the second elevation. Because the distance between the first arterial distension sensor and the second arterial distension sensor is known (it is fixed by way of the housing, for example, housing 302), the monitoring device, and in particular a controller or processing unit of the monitoring device (for example, the controller 412), can calculate at least a first PWV estimate and a second PWV estimate at the first and the second elevations, respectively, based on the first and the second PTT estimates, respectively.

In some specific implementations, the controller 412 can calculate $\Delta P$ via equation 9 based on measurements of $\Delta h$, which can be obtained from one or more elevation sensors (for example, elevation sensor 416). As for $\Delta c$, $\Delta c$ was defined above as the difference $c_+ - c_-$, where $c_+$ denotes the product of the blood density p and the square of the PWV estimate obtained at the second elevation, $c_-$ denotes the product of the blood density $\rho$ and the square of the PWV estimate obtained at the first elevation. As such, the controller can calculate each of $c_-$ and $c_+$ based on the measurements performed by the first and the second arterial distension sensors at the first and the second elevations. Additionally, the controller 412 can calculate $c_h$ based on measurements performed at the reference elevation (for example, at the elevation of the heart). As such, the controller can evaluate equation 14, or evaluate result values based on equation 14 (for example, previously calculated and stored in memory such as in an interpolation table), to determine the value of the stress-strain parameter $P_0$. Notably, while equation 14 is strictly valid for an exponential stress-strain relation, the single stress-strain parameter $P_0$ needed in order to obtain a quantitative relation between PWV and mean arterial pressure also is obtained from differences of the PWV values and differences of the hydrostatic pressures as obtained using measurements from at least two different elevations (the first elevation and the second elevation).

Figure 10:
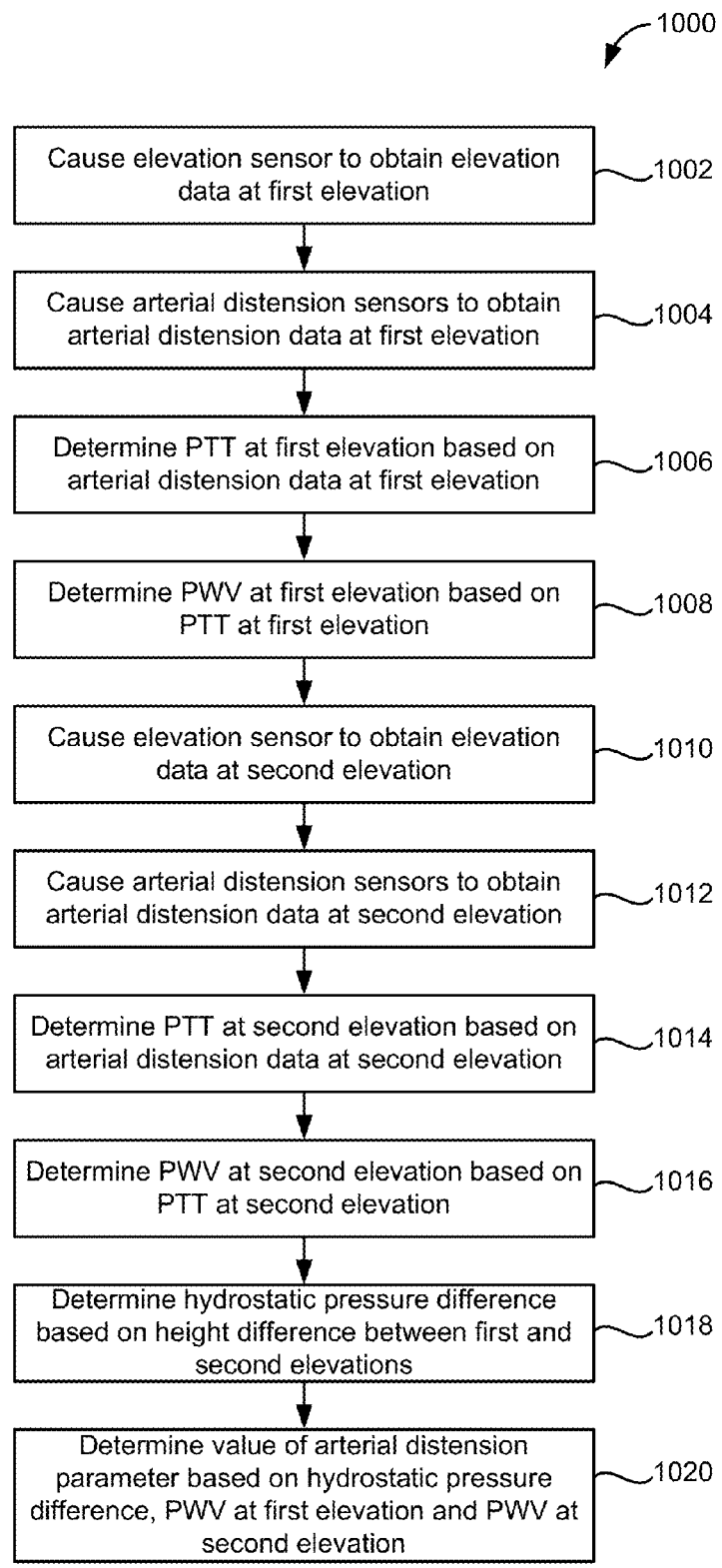
FIG. 10 shows a flow diagram showing an example process for calibrating an ambulatory monitoring device based on hydrostatic pressure according to some implementations.

FIG. 10 shows a flow diagram showing an example process 1000 for calibrating an ambulatory monitoring device based on hydrostatic pressure according to some implementations. For example, the controller 412 can perform (or cause the performance of) process 1000 during an initial hydrostatic calibration of the ambulatory monitoring device 400. Additionally or alternatively, the controller 412 can perform (or cause the performance of) process 1000 during regular operation, for example, on a continuous or periodic basis after an initial hydrostatic calibration is first performed.

In some implementations, for example, during an initial calibration, the process 1000 begins after the controller 412 prepares the monitoring device 400 (for example, including the elevation sensor 416 and at least the first and the second arterial distension sensors 406 and 408) to perform measurements and to obtain sensor data based on the measurements. For example, the controller 412 prepares the elevation sensor 416 to obtain elevation data, and prepares the first and the second arterial distension sensors 406 and 408, respectively, to perform measurements of the arterial distension of the artery of interest and to obtain arterial distension data based on the measurements.

The initial preparation can include, for example, retrieving and loading various control parameters from memory (for example, from memory 418), such as values of the blood density and gravitational acceleration parameters $\rho$ and g, respectively, as well as values of parameters specific to the type of sensors utilized for the first and the second arterial distension sensors 406 and 408. For example, if the first and the second arterial distension sensors 406 and 408 are ultrasound sensors, the preparation can include retrieving or otherwise selecting or determining values of an excitation frequency and amplitude of the pressure wave that will be generated when performing measurements of the arterial distension. Similarly, if the first and the second arterial distension sensors 406 and 408 are PPG sensors, the preparation can include retrieving or otherwise selecting or determining values of an excitation frequency and amplitude of the incident light that will be generated when performing measurements of the arterial distension. Similarly, if the first and the second arterial distension sensors 406 and 408 are bioimpedance sensors, the preparation can include retrieving or otherwise selecting or determining values of an excitation carrier frequency and amplitude of the incident electrical current that will be generated when performing measurements of the arterial distension. In some implementations, the preparation also can include retrieving the value of the distance of separation $\Delta D$ between the first and the second arterial distension sensors 406 and 408.

In some implementations, the process 1000 begins in block 1002 with the controller 412 causing the elevation sensor 416 to obtain elevation data. In some implementations or use cases, block 1002 is performed while the subject wearing the monitoring device 400 positions (or has positioned) the device at a first elevation (for example, below the heart). FIG. 11A shows a diagrammatic representation of a standing subject 1100 wearing an ambulatory monitoring device 400 on a wrist positioned at an elevation 1102 below the subject's heart. While block 1002 is being performed, the subject can hold the device at the first elevation for at least a brief duration of time (for example, 2, 3, 4, 5, 10 or more seconds). The controller 412 also receives the elevation data in block 1002. For example, the controller 412 can receive the elevation data directly from the elevation sensor 416. In some other implementations, the signal processor 414 first receives the elevation data and subsequently passes the elevation data (or processed elevation data) to the controller 412 in block 1002. In some implementations, the controller 412 also determines the first elevation of the monitoring device 400 in block 1002 based on the elevation data. As described above, the first elevation can be determined as an absolute elevation or as a relative elevation (for example, relative to a heart level reference). In some implementations, the first elevation is set to be a reference elevation.

In some implementations, the controller 412 causes each of the first and the second arterial distension sensors 406 and 408 to obtain arterial distension data in block 1004 while the monitoring device 400 is positioned at the first elevation. The controller 412 also receives the arterial distension data in block 1004. For example, the controller 412 can receive the arterial distension data directly from the first and the second arterial distension sensors 406 and 408. In some other implementations, the signal processor 414 first receives the arterial distension data and subsequently passes the arterial distension data (or processed arterial distension data) to the controller 412 in block 1004. In some implementations, the controller 412 also determines an arterial distension waveform in block 1004 based on the arterial distension data.

The process 1000 proceeds in block 1006 with the controller 412 determining a pulse transit time (PTT) based on the arterial distension data obtained at the first elevation. As described above, determining the PTT at the first elevation can include determining a first temporal location of a detected pulse based on the arterial distension data obtained by the first arterial distension sensor 406, determining a second temporal location of the pulse based on the arterial distension data obtained by the second arterial distension sensor 408, and determining the PTT as the temporal distance between the first and the second temporal locations. In some implementations, the process then proceeds in block 1008 with the controller 412 determining a pulse wave velocity (PWV) at the first elevation based on the determined PTT and the value of the known spatial distance $\Delta D$ between the first and the second arterial distension sensors 406 and 408. For example, the controller 412 can calculate the PWV as the quotient of the spatial distance $\Delta D$ divided by the PTT.

In some implementations, the process 1000 proceeds in block 1010 with the controller 412 again causing the elevation sensor 416 to obtain elevation data. However, block 1010 is performed while the subject wearing the monitoring device 400 positions (or has positioned) the device at a second elevation (for example, above the heart). FIG. 11B shows a diagrammatic representation of a standing subject 1100 wearing an ambulatory monitoring device 400 on a wrist positioned at an elevation 1104 above the subject's heart. While block 1010 is being performed, the subject can hold the device at the second elevation for at least a brief duration of time (for example, 2, 3, 4, 5, 10 or more seconds). The controller 412 also receives the elevation data for the second elevation in block 1010. For example, the controller 412 can receive the elevation data directly from the elevation sensor 416. In some other implementations, the signal processor 414 first receives the elevation data and subsequently passes the elevation data (or processed elevation data) to the controller 412 in block 1010. In some implementations, the controller 412 also determines the second elevation of the monitoring device 400 in block 1002 based on the elevation data. As described above, the second elevation can be determined as an absolute elevation or as a relative elevation (for example, relative to a heart level reference or relative to the first elevation).

In some implementations, the controller 412 again causes each of the first and the second arterial distension sensors 406 and 408 to obtain arterial distension data in block 1112 while the monitoring device 400 is positioned at the second elevation. The controller 412 also receives the arterial distension data at the second elevation in block 1012. For example, the controller 412 can receive the arterial distension data directly from the first and the second arterial distension sensors 406 and 408. In some other implementations, the signal processor 414 first receives the arterial distension data and subsequently passes the arterial distension data (or processed arterial distension data) to the controller 412 in block 1004. In some implementations, the controller 412 also determines an arterial distension waveform in block 1012 based on the arterial distension data at the second elevation.

The process 1000 proceeds in block 1014 with the controller 412 determining a second PTT based on the arterial distension data obtained at the second elevation. As described above, determining the PTT at the second elevation can include determining a first temporal location of a second detected pulse based on the arterial distension data obtained by the first arterial distension sensor 406 at the second elevation, determining a second temporal location of the second pulse based on the arterial distension data obtained by the second arterial distension sensor 408 at the second elevation, and determining the second PTT as the temporal distance between the first and the second temporal locations of the second pulse. In some implementations, the process then proceeds in block 1016 with the controller 412 determining a second PWV based on the determined second PTT and the value of the known spatial distance $\Delta D$ between the first and the second arterial distension sensors 406 and 408. For example, the controller 412 can calculate the second PWV as the quotient of the spatial distance $\Delta D$ divided by the second PTT.

In some implementations, the process 1000 proceeds in block 1018 with the controller 412 determining a hydrostatic pressure difference $\Delta P$ based on the height difference $\Delta h$ between the first and the second elevations. For example, the controller 412 can calculate the hydrostatic pressure difference based on equation 9 above using values of the blood density and gravitational acceleration parameters $\rho$ and g, respectively, retrieved from the memory 418.

In some implementations, the process 1000 proceeds in block 1020 with the controller 412 determining a value of the stress-strain parameter based on the hydrostatic pressure difference $\Delta P$, the PWV obtained for the first elevation and the PWV obtained for the second elevation. For example, the controller 412 can calculate the stress-strain parameter $P_0$ using equation 14 above. In implementations in which the first elevation was level with the subject's heart, $c_- = c_h$ and all the parameters needed to determine $P_0$ are thus known. However, in implementations in which the first elevation was below the heart level, the process 1000 can include an additional block (not shown) in which arterial distension data is obtained at the heart level.

In such latter implementations in which the first elevation was not at the heart level, the controller 412 can again cause the elevation sensor 416 to obtain elevation data while the subject wearing the monitoring device 400 positions (or has positioned) the device at a third elevation level with the heart. FIG. 11C shows a diagrammatic representation of a standing subject 1100 wearing an ambulatory monitoring device 400 on a wrist positioned at an elevation 1106 approximately level with the subject's heart. Again, the subject can hold the device at the heart elevation for at least a brief duration of time (for example, 2, 3, 4, 5, 10 or more seconds). The controller 412 also receives the elevation data for the heart elevation in this additional block. For example, the controller 412 can receive the elevation data directly from the elevation sensor 416. In some other implementations, the signal processor 414 first receives the elevation data and subsequently passes the elevation data (or processed elevation data) to the controller 412.

In some implementations, the controller 412 again causes each of the first and the second arterial distension sensors 406 and 408 to obtain arterial distension data while the monitoring device 400 is positioned at the heart elevation. The controller 412 also receives the arterial distension data at the heart elevation in this additional block. Again, the controller 412 can receive the arterial distension data directly from the first and the second arterial distension sensors 406 and 408 or can receive the arterial distension data from the signal processor. In some implementations, the controller 412 also determines an arterial distension waveform based on the arterial distension data at the heart elevation.

In some implementations, the controller 412 then determines a third PTT based on the arterial distension data obtained at the heart elevation. As described above, determining the PTT at the heart elevation can include determining a first temporal location of a third detected pulse based on the arterial distension data obtained by the first arterial distension sensor 406 at the heart elevation, determining a second temporal location of the third pulse based on the arterial distension data obtained by the second arterial distension sensor 408 at the heart elevation, and determining the third PTT as the temporal distance between the first and the second temporal locations of the third pulse. In some implementations, the process then proceeds with the controller 412 determining a third PWV based on the determined third PTT and the value of the known spatial distance ΔD between the first and the second arterial distension sensors 406 and 408. For example, the controller 412 can calculate the third PWV as the quotient of the spatial distance ΔD divided by the third PTT. The controller 412 can then calculate the stress-strain parameter $P_0$ using equation 14 above.

Although the foregoing description for identifying $P_0$ was primarily described as relying on a first measurement at a first elevation below the heart and a second measurement at a second elevation above the heart, it is not necessary that the first elevation be below the heart and the second elevation be above the heart. For example, one of the first elevation or the second elevation can be at the level of the heart as briefly described above. As another example, both of the first and the second elevations can be above the heart. As another example, both of the first and the second elevations can be below the heart. However, the use of a first elevation below the heart and a second elevation above the heart can be desirable if the assumed stress-strain relation (for example, shown in equation 1) deviates from the model.

In some implementations, the controller 412 can be triggered to perform the process 1000 in an initial hydrostatic pressure calibration responsive to the monitoring device 400 being turned on, reset or enabled, responsive to the controller determining that calibration has been lost or that the accuracy of the blood pressure estimates have been degraded, or responsive to being triggered by a user (whether the user is a subject wearing the monitoring device or a doctor or other medical professional providing or setting up the monitoring device for a subject). In some implementations, the controller 412 can recalibrate or update the value of the stress-strain parameter $P_0$ using the process 1000 periodically (for example, every hour or every few hours), at particular times of the day, or after a particular number of measurements, among other suitable or desirable intervals.

In some implementations, the monitoring device 400 can include a display, one or more lights (for example, LEDs) or one or more sound-producing devices to alert the subject wearing the device to position and hold the device at the different elevations to enable the calibration (or recalibration).

In some implementations, the controller 412 (and the monitoring device 400 in general) can be configured to operate in a calibration mode and a normal operating mode. For example, the hydrostatic pressure calibration just described with reference to the process 1000 can be performed while in the calibration mode, for example, during an initialization operation responsive to the monitoring device 400 being turned on, reset or enabled, responsive to the controller determining that calibration has been lost or that the accuracy of the blood pressure estimates have been degraded, or responsive to being triggered by a user (whether the user is a subject wearing the monitoring device or a doctor or other medical professional providing or setting up the monitoring device for a subject). Conversely, while operating in the normal mode, the controller 412 may or may not validate the value of the stress-strain parameter $P_0$ and recalibrate as needed. In some other implementations, the controller 412, and the monitoring device 400 in general, can operate in a single operating mode in which measurements of the relative or absolute elevation of the monitoring device are performed in conjunction with the measurements of the distension signal by each of the first and the second arterial distension sensors 406 and 408. In such implementations, the controller 412 can recalibrate (update) the value of the stress-strain parameter $P_0$ continuously or periodically, for example, with each subsequent estimation of the PWV (and each accompanying estimation of the transmural blood pressure). In some other implementations, the controller 412 can at least determine whether the value of the stress-strain parameter $P_0$ is valid with each subsequent estimation of the PWV (and each accompanying estimation of the transmural blood pressure). In some such latter implementations, to determine whether the stress-strain parameter $P_0$ is still valid, the controller 412 can be operable to determine whether the pulse pressure is sufficiently level or relatively constant (for example, within a threshold deviation), whether the pulse rate (number of pulses per unit time) has increased or decreased beyond a threshold, or whether the estimated blood pressure has changed appreciable over a relatively short duration of time, among other metrics that may be suitable for use in determining whether the arterial properties have changed appreciably.

PTT Estimation Using Cross-Correlation

Although various implementations presented above were described with reference to implementations in which the PTT is estimated based on a temporal difference between first and second temporal locations associated with the detections of a pulse at first and second physical locations along a segment of an artery, in some other implementations, other techniques, methods or processes can additionally or alternatively be used to estimate the PTT for use in calculating PWV and estimating blood pressure based on the PWV. For example, a robust method for estimating PTT can be based on a cross-correlation of two arterial distension signals (each including a sequence of pulses). For example, the first arterial distension signal including the first sequence of pulses can be determined by the controller 412 based on the arterial distension data obtained from the first arterial distension sensor 406, and the second arterial distension signal including the second sequence of pulses can be determined by the controller 412 based on the arterial distension data obtained from the second arterial distension sensor 408.

Figure 12A:
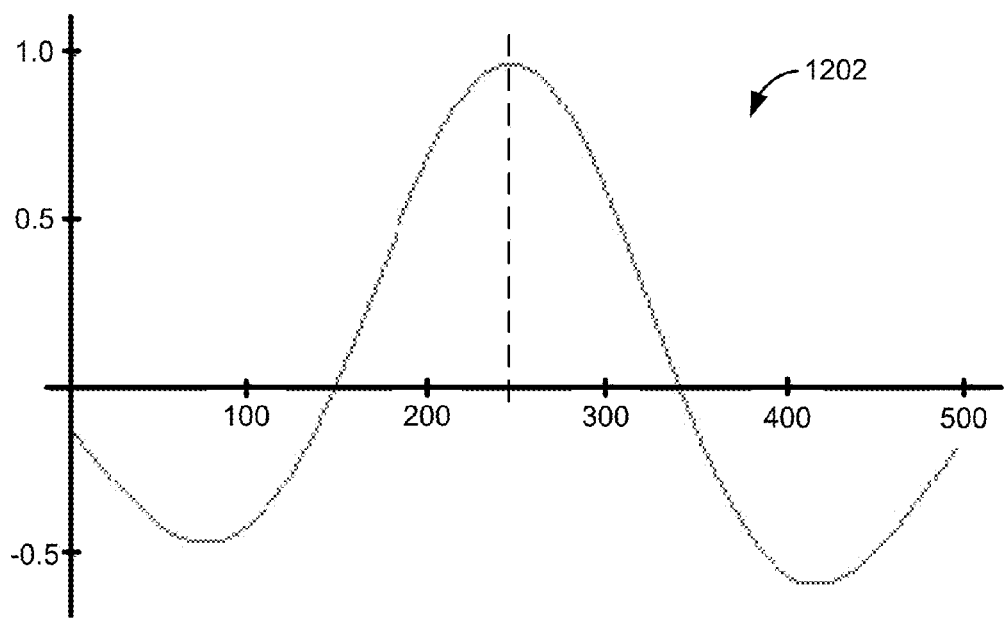
FIG. 12A shows an example plot of correlation data as a function of time delay between two example linearly-filtered signals of the type shown in FIG. 9B.
Figure 12B:
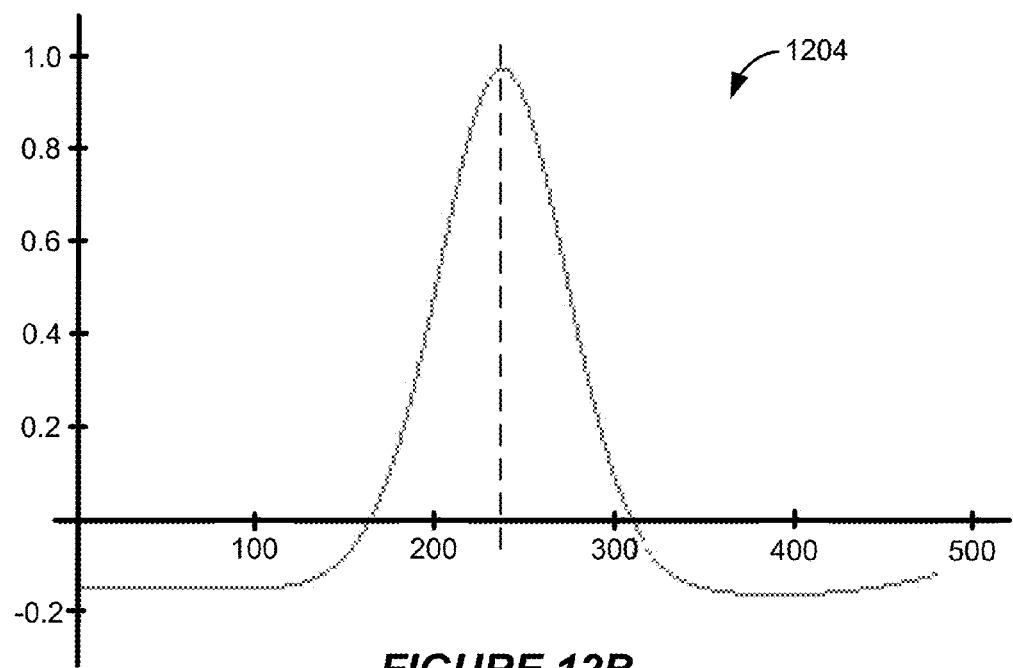
FIG. 12B shows an example plot of correlation data as a function of time delay between two example nonlinearly-processed signals of the type shown in FIG. 9C.

In some implementations, the controller performs the cross-correlation operation on filtered or otherwise pre-processed versions of the first and the second arterial distension signals. For example, the controller 412 can perform the cross-correlation operation on the first and the second arterial distension signals as, for example, filtered as described above with reference to FIG. 9B. FIG. 12A shows an example plot 1202 of correlation data as a function of time delay between two example linearly-filtered signals of the type shown in FIG. 9B. The time delay corresponds to the temporal displacement in the correlation calculation resulting from the use of the two different arterial distension sensors 406 and 408 at the two different physical locations along the artery of interest. In particular, the maximum of the correlation data corresponds to the PTT. In some other implementations, the controller performs the cross-correlation operation on nonlinearly-processed versions of the first and the second arterial distension signals. For example, the controller 412 can perform the cross-correlation operation on the first and the second arterial distension signals as, for example, nonlinearly-processed as described with reference to FIG. 9C. FIG. 12B shows an example plot 1204 of correlation data as a function of time delay between two example nonlinearly-processed signals of the type shown in FIG. 9C. Again, the time delay generally refers to the temporal displacement in the correlation calculation resulting from the use of the two different arterial distension sensors 406 and 408 at the two different physical locations along the artery of interest, and the maximum of the correlation data corresponds to the PTT.

The maximum normalized correlation is close to 1 for each of the correlation plots 1202 and 1204 (0.967 and 0.971, respectively), which implies that the arterial distension signals obtained by the first arterial distension sensor 406 at the first physical location have essentially an identical shape as the arterial distension signals obtained by the second arterial distension sensor 408 at the second physical location, although the two arterial distension signals do not necessarily have identical amplitudes. As shown in the correlation plot 1204 shown in FIG. 12B, the nonlinear-processing operations performed on the filtered arterial distension signals enhance the weight of the larger amplitudes and larger gradients. While there is a very small difference between the positions of the correlation maxima (about 0.1 ms) when comparing FIGS. 12A and 12B, because the nonlinearly-processed arterial distension signals result in the greatest degree of correlation (for example, as evidenced by the narrower width of the peak in the correlation plot 1204), the time delay, and thus the estimated PTT, will also be the most reliable for the nonlinearly-processed arterial distension signals.

As just described, the controller 412 can estimate the PTT between the first and the second physical locations based on the time delay associated with the maximum of the correlation data obtained for a plot of correlation data versus time delay (such as one of the correlation plots 1202 or 1204 shown in FIG. 12A and FIG. 12B). Generally, finding the maximum of a correlation curve (indicated with the vertical dotted lines in FIGS. 12A and 12B) involves differentiation. However, differentiation generally enhances noise. In some implementations, to avoid enhancing noise, the controller 412 utilizes a Hilbert transform to identify the maximum of the correlation curve. The utilization of a Hilbert transform provides a more robust method for identifying the maxima that does not involve noise enhancement. For reference, a Hilbert transform of an even function provides for an uneven function that has a zero crossing at the same location as the derivative of the even function. If the function is slightly uneven there may be a discrepancy. Unevenness of the correlation plot 1202 or 1204 can occur if the pulses at the first and the second physical locations do not have the same shape (for example, as a result of propagation dispersion). Using the position of the maximum of a slightly uneven function will in general imply a bias error. The use of a Hilbert transform reduces such error, and as described above, does not enhance the effects of noise.

Timing of Individual Pulses

Figure 13:
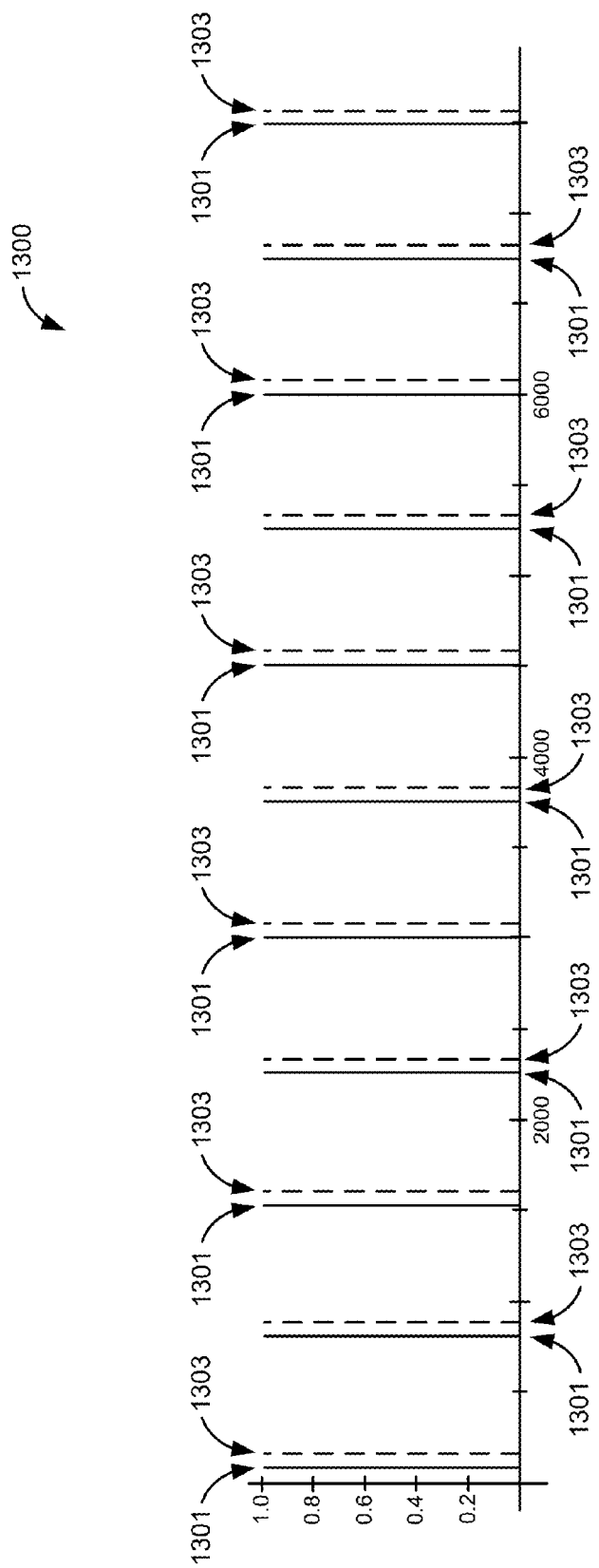
FIG. 13 shows a plot of an example timing of individual pulses in an example artery.

In some other implementations, the controller 412 can additionally or alternatively examine correlation between individual pulses, for example, pulses obtained from the same sensor. For example, this procedure can advantageously be used to validate individual pulses before PTT estimation. Pulses that are corrupted (for example, by limb movements) can be ignored or neglected when estimating the PTT. FIG. 13 shows a plot of an example timing of individual pulses in an example artery. Each of the peaks 1301 corresponds to the temporal location of a respective pulse as determined from arterial distension data obtained from the first arterial distension sensor 406 at the first physical location; each of the peaks 1303 corresponds to the temporal location of the respective pulse as determined from arterial distension data obtained from the second arterial distension sensor 408 at the second physical location. The horizontal axis is defined in milliseconds (ms). The temporal distance between a given pair of neighboring pulses 1301 and 1303 represents the PTT.

Pulse Wave Velocity from Distension and Flow

Figure 14:
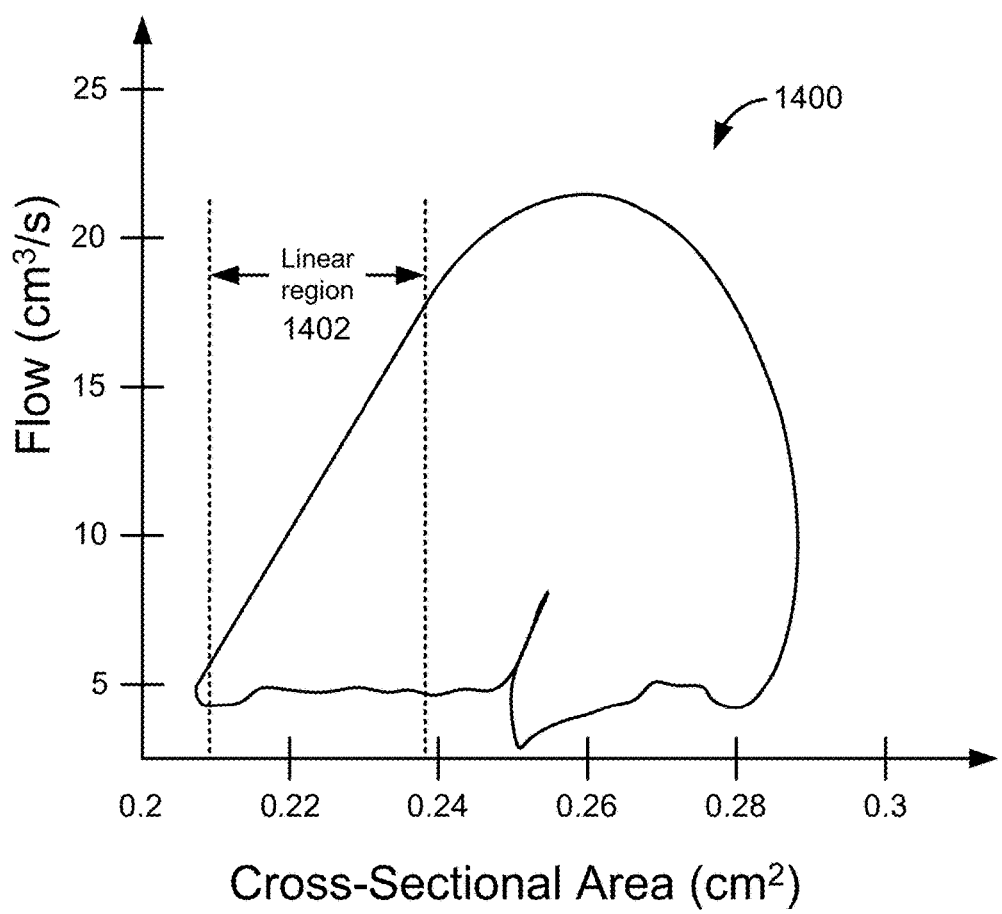
FIG. 14 shows a plot of typical changes in blood flow in an example artery versus cross-sectional area during a cardiac cycle.

In some implementations, the PWV also can be obtained by an indirect method as an alternative to performing PTT calculations using the timing of pulses at two physical locations. Some such implementations are based on time resolved joint measurements of flow and distension during a pulse. In particular, an approximately linear relation between blood flow and cross-sectional area of the artery exists during the systolic part of the pulse and the slope of this linear relation provides for an estimate of the PWV. FIG. 14 shows a plot 1400 of typical changes in blood flow in an example artery versus cross-sectional area during a cardiac cycle. As just described, the controller 412 can estimate the PWV from the linear region 1402 of the plot 1400. For example, the controller can identify the linear region 1402 by determining a derivative of some or all of the data. The linear region 1402 is characterized by a portion of the data whose derivative is approximately constant.

Figure 15:
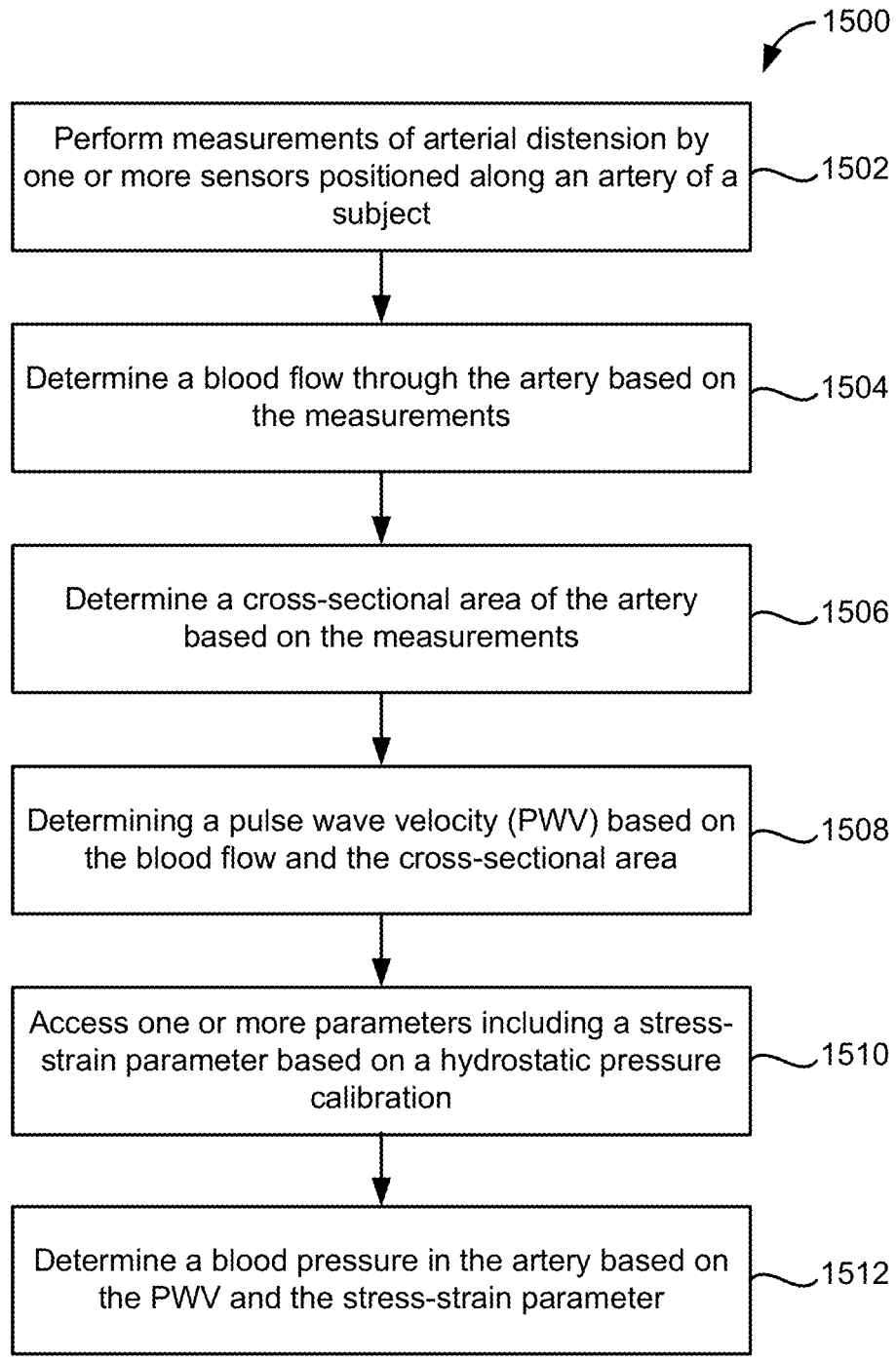
FIG. 15 shows a flow diagram showing an example process for estimating blood pressure based on pulse wave velocity (PWV) according to some implementations.

FIG. 15 shows a flow diagram showing an example process 1500 for estimating blood pressure based on PWV according to some implementations. In some implementations, the process 1500 makes use of the relationship expressed in equation 6. In various implementations, the controller 412 can perform (or cause the performance of) process 1500 continuously. For example, the controller 412 can cause the performance of process 1500 periodically, such as every 2, 3, 4, 5, 10 or more seconds, every minute, every few minutes, every hour or every few hours, or at other suitable or desirable intervals.

In some implementations, the process 1500 begins after the controller 412 prepares the monitoring device 400, and specifically at least one sensor, to perform measurements and to obtain sensor data based on the measurements. For example, the controller 412 prepares at least one sensor (for example, the same or similar to the first and the second arterial distension sensors 406 and 408) to perform measurements of the arterial distension of the artery of interest and to obtain arterial distension data based on the measurements. In some implementations, the controller 412 also prepares the elevation sensor 416 to obtain elevation data associated with the elevation of the monitoring device 400 (for example, an absolute elevation or an elevation relative to a reference elevation such as the heart level). The initial preparation can include, for example, retrieving and loading various control parameters from memory (for example, from memory 418), such as a value of the arterial stress-strain parameter $P_0$. Other values that can be retrieved and loaded from the memory 418 include, for example, a value of the blood density p as well as values of parameters specific to the type of sensor utilized.

In some implementations, the process 1500 begins in block 1502 with performing measurements of arterial distension by one or more sensors positioned along an artery of the subject. For example, the controller 412 can cause at least one arterial distension sensor to obtain the measurements of the arterial distension data. The controller 412 also receives the arterial distension data from the at least one arterial distension sensor in block 1502. For example, the controller 412 can receive the arterial distension data directly from the arterial distension sensor. In some other implementations, the signal processor 414 first receives the arterial distension data and subsequently passes the arterial distension data (or processed arterial distension data) to the controller 412 in block 1502. In some implementations, the controller 412 also determines an arterial distension waveform in block 1502 based on the arterial distension data.

The process 1500 proceeds in block 1504 with determining blood flow through the artery based on the measurements performed in block 1502. For example, the controller 412 can determine the blood flow based on the measurements of the arterial distension data. In some implementations, the process 1500 then proceeds in block 1506 with the controller 412 determining a cross-sectional area A of the artery based on the measurements. In some implementations, the process then proceeds in block 1508 with the controller 412 determining a PWV based on the determined blood flow and the determined cross-sectional area A. For example, as described above with reference to FIG. 14, the controller 412 can estimate the PWV from a linear region of a plot of blood flow versus cross-sectional area. For example, the controller can identify the linear region of the flow data by determining a derivative of some or all of the flow data. As described above, the linear region is characterized by a portion of the flow data whose derivative is approximately constant. The controller can estimate the value of the PWV as the value of the constant portion of the derivative.

In some implementations, the process 1500 proceeds in block 1510 with the controller 412 accessing the stress-strain parameter $P_0$. In implementations in which the value of the arterial stress-strain parameter $P_0$ was earlier retrieved from the memory 418, accessing the arterial stress-strain parameter $P_0$ can simply include accessing the value of the arterial stress-strain parameter $P_0$ from a random access memory (RAM) included within or connected with the controller 412. In some implementations, the process 1500 then proceeds in block 1512 with the controller 412 determining an estimate of the blood pressure P in the artery of the subject based on the PWV and the value of the stress-strain parameter $P_0$. For example, the controller 412 can calculate or otherwise determine the blood pressure P of the subject based on the PWV and $P_0$ based on the relationship expressed in Equation 6. As described above, the mean transmural blood pressure P can be expressed as a function of PWV using equation 6. In some implementations, the controller 412 can be configured to use an analytical or numerical solution to solve for the mean transmural blood pressure P based on the PWV determined in block 1508. In some other implementations, a numerical solution can be previously ascertained by another processing system such as an external computing system. In such latter implementations, the results of the numerical solution can then be programmed into the memory 418, for example, as a lookup table, at the end of the manufacturing process. In some such implementations, not all values of PWV and blood pressure P need be programmed because the controller 412 can be configured to perform interpolation between values.

In some implementations, the controller 412 also causes the elevation sensor 416 to obtain elevation data in block 1502 concurrently, periodically, intermittently or in parallel with the obtainment of the arterial distension data. As described above, the elevation of the monitoring device 400 can be determined as an absolute elevation or as a relative elevation (for example, relative to a heart level reference or relative to a previous elevation). In such implementations, if the controller 412 determines that the elevation at which the arterial distension data used to determine the PWV is not at the heart level, the controller 412 can apply a correction for the difference in hydrostatic pressure at the elevation at which the arterial distension data is measured relative to the heart level.

Detailed Example of Initialization and Calibration

Figure 16:
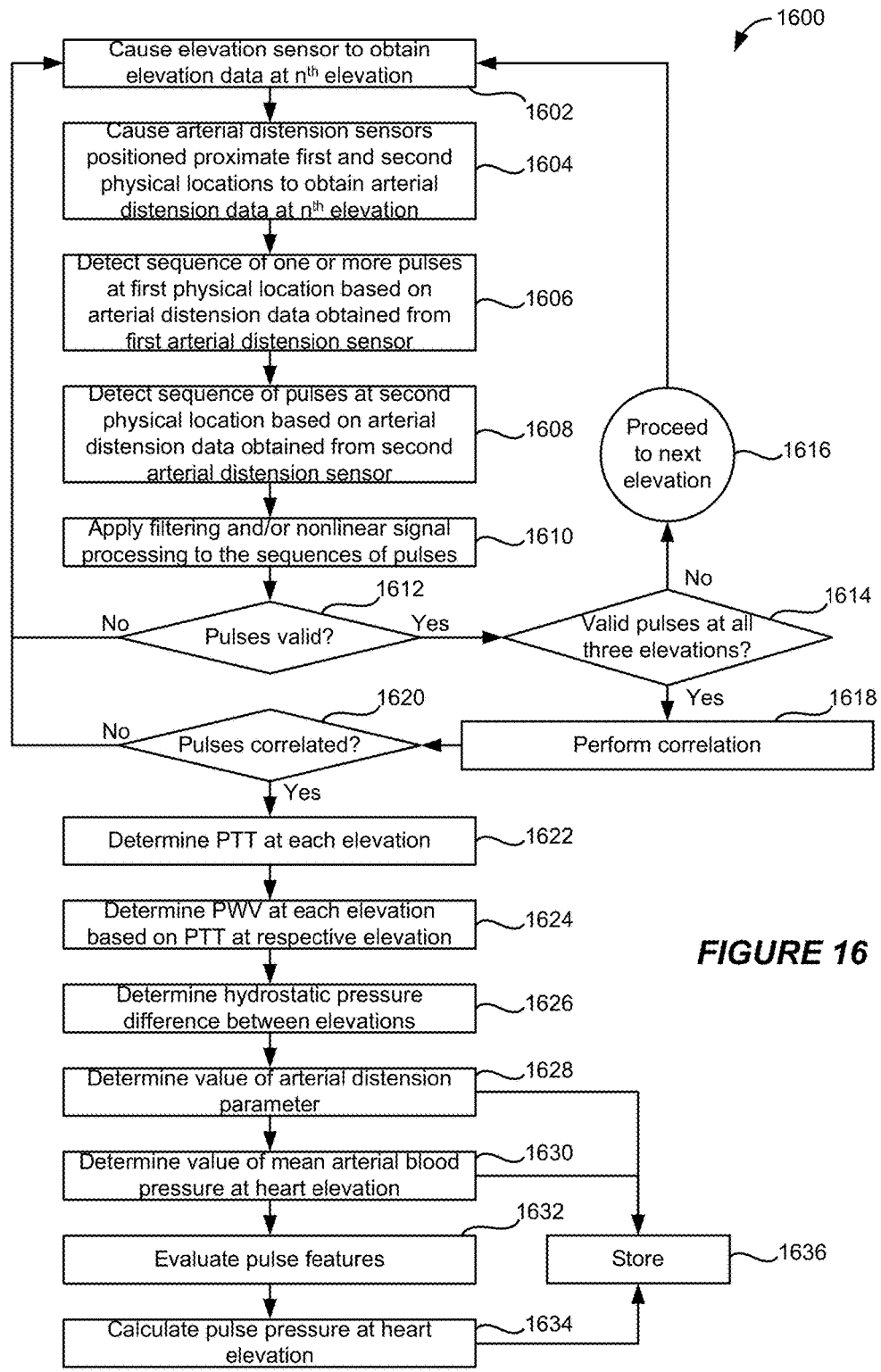
FIG. 16 shows a flow diagram showing an example process for calibrating an ambulatory monitoring device based on hydrostatic pressure according to some implementations.
Figure 17:
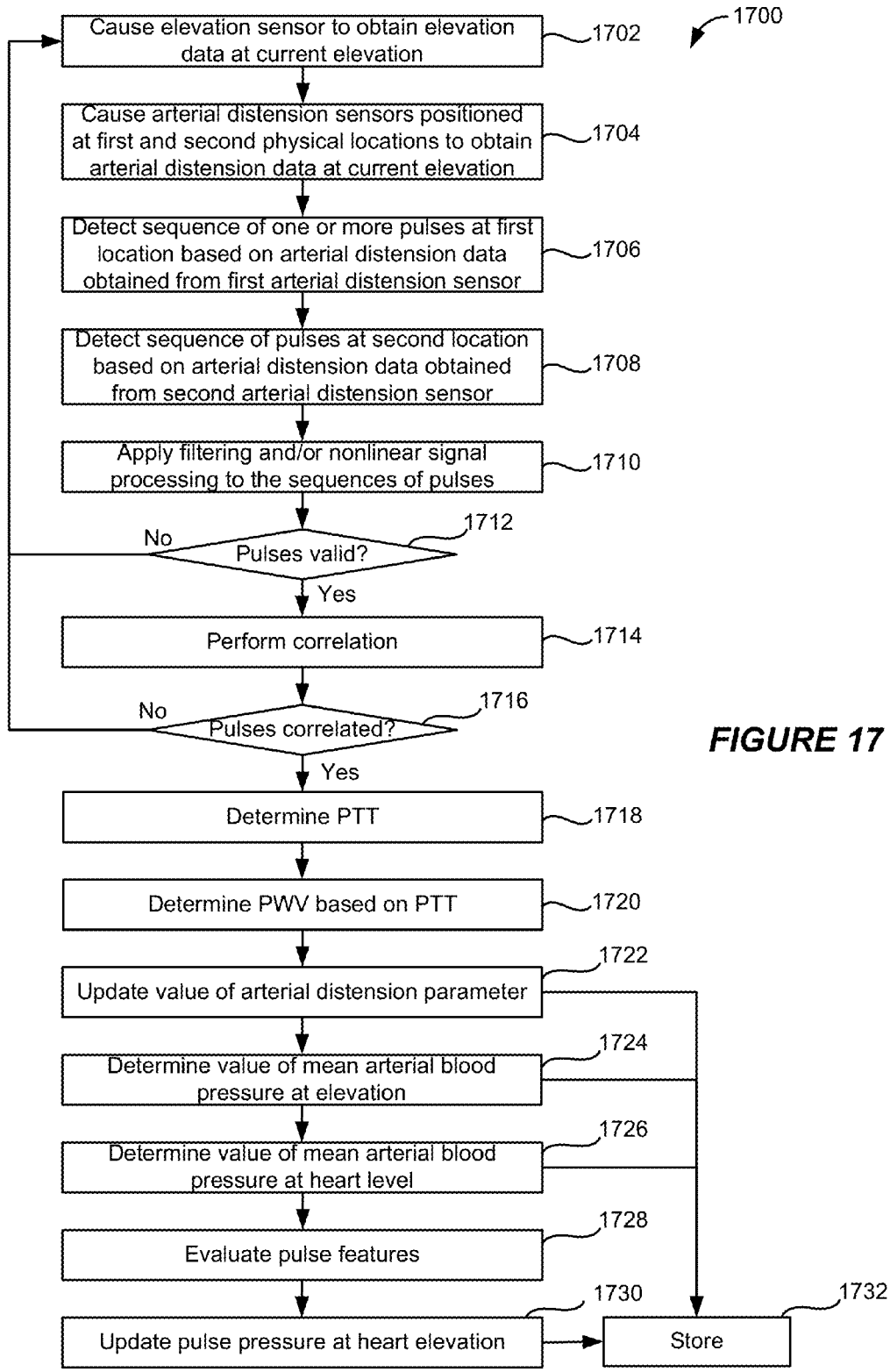
FIG. 17 shows a flow diagram showing an example process for estimating blood pressure based on pulse wave velocity (PWV) according to some implementations.

FIG. 16 shows a flow diagram showing an example process 1600 for calibrating an ambulatory monitoring device based on hydrostatic pressure according to some implementations. For example, the controller 412 can perform (or cause the performance of) process 1600 during an initialization mode, stage, phase or process of the ambulatory monitoring device 400. In some implementations, the controller 412 can be triggered to perform the process 1600 responsive to the monitoring device 400 being turned on, reset or enabled, responsive to the controller determining that calibration has been lost or that the accuracy of the blood pressure estimates have been degraded, or responsive to being triggered by a user (whether the user is a subject wearing the monitoring device or a doctor or other medical professional providing or setting up the monitoring device for a subject).

In some implementations, the process 1600 begins after the controller 412 prepares the monitoring device 400 (for example, including the elevation sensor 416 and at least the first and the second arterial distension sensors 406 and 408) to perform measurements and to obtain sensor data based on the measurements. For example, the controller 412 prepares the elevation sensor 416 to obtain elevation data, and prepares the first and the second arterial distension sensors 406 and 408, respectively, to perform measurements of the arterial distension of the artery of interest and to obtain arterial distension data based on the measurements.

The initial preparation can include, for example, retrieving and loading various control parameters from memory including values of the blood density and gravitational acceleration parameters ρ and g, respectively, as well as values of parameters specific to the type of sensors utilized for the first and the second arterial distension sensors 406 and 408. In some implementations, the preparation also can include retrieving the value of the distance of separation ΔD between the first and the second arterial distension sensors 406 and 408.

In some implementations, the process 1600 begins in block 1602 with the controller 412 causing the elevation sensor 416 to obtain elevation data at an $n^{th}$ elevation, beginning with a first elevation. In other words, block 1602 is first performed while the subject wearing the monitoring device 400 positions (or has positioned) the device at the first elevation (for example, below the heart). The controller 412 or the signal processor 414 also receives the elevation data in block 1602. For example, the controller 412 can receive the elevation data directly from the elevation sensor 416. In some other implementations, the signal processor 414 first receives the elevation data and subsequently passes the elevation data (or processed elevation data) to the controller 412 in block 1602. In some implementations, the controller 412 also determines the first elevation of the monitoring device 400 in block 1602 based on the elevation data. As described above, the first elevation can be determined as an absolute elevation or as a relative elevation (for example, relative to a heart level reference). In some implementations, the first elevation is set to be a reference elevation.

In some implementations, the process 1600 proceeds in block 1604 with the controller 412 causing each of the first and the second arterial distension sensors 406 and 408 to obtain arterial distension data while the monitoring device 400 is positioned at the first elevation. The controller 412 or the signal processor 414 receives the arterial distension data obtained from the first arterial distension sensor 406 and detects a sequence of one or more pulses based on the arterial distension data in block 1606. In block 1608, the controller 412 or the signal processor 414 receives the arterial distension data obtained from the second arterial distension sensor 408 and detects the sequence of pulses based on the arterial distension data. That is, the controller 412 or the signal processor 414 detects the sequence of pulses at each of the first and the second physical locations using the arterial distension data obtained from the respective first or second arterial distension sensor 406 or 408.

In some implementations, the process 1600 proceeds in block 1610 with the controller 412 or the signal processor 414 applying or performing one or more linear or nonlinear filtering or other linear or nonlinear signal processing operations on the two sequences of pulses. For example, the controller 412 or the signal processor 414 can apply or perform any one or more of the linear or nonlinear filtering or other linear or nonlinear signal processing operations described above with reference to the process 800 of FIG. 8 or the examples described with reference to FIGS. 9A-9C. In some implementations, the signal processor 414 can receive the arterial distension data from the first and the second arterial distension sensors 406 and 408 in block 1604, detect the two sequences of pulses in blocks 1606 and 1608, perform the linear or nonlinear filtering or other linear or nonlinear signal processing operations on the two sequences of pulses in block 1610 and subsequently pass the processed sequences to the controller 412. In some other implementations in which the signal processor 414 is included within or implemented by the controller 412, the controller 412 can receive the arterial distension data from the first and the second arterial distension sensors 406 and 408 in block 1604, detect the two sequences of pulses in blocks 1606 and 1608, and perform the linear or nonlinear filtering or other linear or nonlinear signal processing operations on the two sequences of pulses in block 1610.

In some implementations, the process 1600 proceeds in block 1612 with the controller 412 determining whether the pulses in each of the two sequences are valid. As described above, pulses can be corrupted, for example, by limb movements. In some implementations, if the one or more pulses from each sequence of pulses are corrupted or otherwise not valid, the process 1600 can return to block 1602. In some implementations, if the pulses are valid, the process proceeds to block 1614 with the controller 412 determining whether valid pulses have been obtained at three distinct elevations. If valid pulses have not been obtained at each of the three distinct elevations, the process 1600 proceeds to the next elevation in 1616 and returns to block 1602 to obtain sensor data at the next elevation (for example, at or above the heart level). For example, the controller 412 can signal the subject to position the monitoring device 400 at the next elevation. In some implementations, the monitoring device 400 can include a display, one or more lights (for example, LEDs) or one or more sound-producing devices to alert the subject wearing the device to position and hold the device at the different elevations to enable the calibration (or recalibration).

If the controller 412 determines in block 1614 that valid pulses have been obtained at all three elevations, the process 1600 proceeds in block 1618 with the controller 412 performing a correlation operation on the two sequences of pulses at each of the three elevations. In some implementations, the process 1600 proceeds in block 1620 with the controller 412 determining whether the pulses in the two sequences of pulses are correlated for the given elevation. In some implementations, if the results of the correlation operation indicate that the pulses are not correlated (for example, indicating motion, respiration or other artifacts), the process 1600 returns to block 1602. In some implementations, if the results of the correlation operation indicate that the pulses are correlated, the process proceeds to block 1622 with the controller 412 determining a PTT at each of the three elevations, for example, in the manner described above with reference to block 808 of the process 800 shown in FIG. 8 or blocks 1006 and 1014 of the process 1000 shown in 10. In some implementations, the process 1600 then proceeds in block 1624 with the controller 412 determining a PWV at each of the three elevations, for example, in the manner described above with reference to block 810 of the process 800 shown in FIG. 8 or blocks 1008 and 1016 of the process 1000 shown in 10.

In some implementations, the process 1600 proceeds in block 1626 with the controller 412 determining a hydrostatic pressure difference $\Delta P$ based on the height difference $\Delta h$ between the first and the second elevations (and/or between the first and the third elevations and/or between the second and the third elevations). For example, the controller 412 can calculate the hydrostatic pressure difference $\Delta P$ based on equation 9 above, as described with reference to block 1018 of the process 1000 shown in FIG. 10, using values of the blood density and gravitational acceleration parameters $\rho$ and $g$, respectively, retrieved from the memory 418. In some implementations, the process 1600 proceeds in block 1628 with the controller 412 determining a value of the arterial stress-strain parameter $P_0$ based on the hydrostatic pressure difference $\Delta P$ and the PWV estimates obtained for the different elevations using equation 14 above as described with reference to block 1020 of the process 1000 shown in FIG. 10.

In some implementations, the process 1600 proceeds in block 1630 with the controller 412 determining an estimate of the mean arterial blood pressure P of the subject at the heart level based on the PWV obtained at the heart level and the value of the arterial stress-strain parameter $P_0$. For example, the controller 412 can calculate or otherwise determine the blood pressure P of the subject based on the PWV and $P_0$ based on the relationship expressed in Equation 6. As described above, the mean transmural blood pressure P can be expressed as a function of PWV using equation 6. In some implementations, the controller 412 can be configured to use an analytical or numerical solution to solve for the mean transmural blood pressure P based on the PWV. In some other implementations, a numerical solution can be previously ascertained by another processing system such as an external computing system. In such latter implementations, the results of the numerical solution can then be programmed into the memory 418, for example, as a lookup table, at the end of the manufacturing process.

In some implementations, the process 1600 proceeds in block 1632 with the controller 412 analyzing the value of the mean arterial blood pressure P as well as the features of the pulses used in the determination of the mean arterial blood pressure P. For example, block 1632 can include identifying the location and amplitude of the peak associated with the systolic pressure, identifying the amplitude of the lowest valley associated with the diastolic pressure, and in some implementations, determining the infinity pressure. In some implementations, the process 1600 proceeds in block 1634 with the controller 412 calculating the pulse pressure at the heart elevation based on the pulse features. In some implementations, the process 1600 proceeds in block 1636 with the controller 412 storing the values of the arterial stress-strain parameter $P_0$, the mean arterial blood pressure P and the pulse pressure.

Detailed Example of Normal Operation with Blood Pressure Estimation

FIG. 16 shows a flow diagram showing an example process 1700 for estimating blood pressure based on pulse wave velocity (PWV) according to some implementations. For example, the controller 412 can perform (or cause the performance of) process 1700 during a normal operation mode, stage, phase or process of the ambulatory monitoring device 400. In some implementations, the controller 412 can cause the performance of process 1700 periodically, such as every 2, 3, 4, 5, 10 or more seconds, every minute, every few minutes, every hour or every few hours, or at other suitable or desirable intervals.

In some implementations, the process 1700 begins in block 1702 with the controller 412 causing the elevation sensor 416 to obtain elevation data at a current elevation of the ambulatory monitoring device 400. The controller 412 or the signal processor 414 also receives the elevation data in block 1702. For example, the controller 412 can receive the elevation data directly from the elevation sensor 416. In some other implementations, the signal processor 414 first receives the elevation data and subsequently passes the elevation data (or processed elevation data) to the controller 412 in block 1702. In some implementations, the controller 412 also determines the value of the current elevation of the monitoring device 400 in block 1702 based on the elevation data. As described above, the current elevation can be determined as an absolute elevation or as a relative elevation (for example, relative to a heart level reference).

In some implementations, the process 1700 proceeds in block 1704 with the controller 412 causing each of the first and the second arterial distension sensors 406 and 408 to obtain arterial distension data while the monitoring device 400 is positioned at the current elevation. The controller 412 or the signal processor 414 receives the arterial distension data obtained from the first arterial distension sensor 406 and detects a sequence of one or more pulses based on the arterial distension data in block 1706. In block 1708, the controller 412 or the signal processor 414 receives the arterial distension data obtained from the second arterial distension sensor 408 and detects the sequence of pulses based on the arterial distension data. That is, the controller 412 or the signal processor 414 detects the sequence of pulses at each of the first and the second physical locations using the arterial distension data obtained from the respective first or second arterial distension sensor 406 or 408.

In some implementations, the process 1700 proceeds in block 1710 with the controller 412 or the signal processor 414 applying or performing one or more linear or nonlinear filtering or other linear or nonlinear signal processing operations on the two sequences of pulses. For example, the controller 412 or the signal processor 414 can apply or perform any one or more of the linear or nonlinear filtering or other linear or nonlinear signal processing operations described above with reference to the process 800 of FIG. 8 or the examples described with reference to FIGS. 9A-9C. In some implementations, the signal processor 414 can receive the arterial distension data from the first and the second arterial distension sensors 406 and 408 in block 1704, detect the two sequences of pulses in blocks 1706 and 1708, perform the linear or nonlinear filtering or other linear or nonlinear signal processing operations on the two sequences of pulses in block 1710 and subsequently pass the processed sequences to the controller 412. In some other implementations in which the signal processor 414 is included within or implemented by the controller 412, the controller 412 can receive the arterial distension data from the first and the second arterial distension sensors 406 and 408 in block 1704, detect the two sequences of pulses in blocks 1706 and 1708, and perform the linear or nonlinear filtering or other linear or nonlinear signal processing operations on the two sequences of pulses in block 1710.

In some implementations, the process 1700 proceeds in block 1712 with the controller 412 determining whether the pulses in each of the two sequences are valid. As described above, pulses can be corrupted, for example, by limb movements. In some implementations, if the one or more pulses from each sequence of pulses are corrupted or otherwise not valid, the process 1700 can return to block 1702. In some implementations, if the pulses are valid, the process proceeds to block 1714 with the controller 412 performing a correlation operation on the two sequences of pulses. In some implementations, the process 1700 proceeds in block 1716 with the controller 412 determining whether the pulses are correlated. In some implementations, if the results of the correlation operation indicate that the pulses are not correlated, the process 1700 returns to block 1702. In some implementations, if the results of the correlation operation indicate that the pulses are correlated, the process proceeds to block 1718 with the controller 412 determining a PTT, for example, in the manner described above with reference to block 808 of the process 800 shown in FIG. 8.

In some implementations, the process 1700 then proceeds in block 1720 with the controller 412 determining a PWV based on the PTT estimate, for example, in the manner described above with reference to block 810 of the process 800 shown in FIG. 8. In some implementations, the process 1700 proceeds in block 1722 with the controller 412 determining or updating the value of the arterial stress-strain parameter $P_0$ based on the hydrostatic pressure difference $\Delta P$ between the current elevation and a previous elevation as well as the PWV estimates obtained for the current and previous elevations (for example, using equation 14 above as described with reference to blocks 1018 and 1020 of the process 1000 shown in FIG. 10).

In some implementations, the process 1700 proceeds in block 1724 with the controller 412 determining an estimate of the mean arterial blood pressure P of the subject at the current elevation based on the PWV obtained at the current elevation and the value of the updated arterial stress-strain parameter $P_0$. For example, the controller 412 can calculate or otherwise determine the blood pressure P of the subject based on the PWV and $P_0$ based on the relationship expressed in Equation 6 as described above with reference to block 814 of the process 800 shown in FIG. 8. In some implementations, the process 1700 proceeds in block 1726 with the controller 412 determining an estimate of the mean arterial blood pressure P of the subject at the heart level based on the value of the mean arterial blood pressure P determined at the current elevation. For example, and as described above, if the controller 412 determines that the current elevation is not at the heart level, the controller 412 can apply a correction for the difference in hydrostatic pressure at the current elevation relative to the heart level.

In some implementations, the process 1700 proceeds in block 1728 with the controller 412 analyzing the value of the mean arterial blood pressure P at the heart level as well as the features of the pulses used in the determination of the mean arterial blood pressure P. For example, block 1728 can include identifying the location and amplitude of the peak associated with the systolic pressure, identifying the amplitude of the lowest valley associated with the diastolic pressure, and in some implementations, determining the infinity pressure. In some implementations, the process 1700 proceeds in block 1730 with the controller 412 calculating and updating the pulse pressure at the heart elevation based on the pulse features. In some implementations, the process 1700 proceeds in block 1732 with the controller 412 storing the updated value of the arterial stress-strain parameter $P_0$, the mean arterial blood pressure P at the current elevation, the mean arterial blood pressure P at the heart level, and the updated pulse pressure.

Generalizations of the Stress-Strain Relationship

Figure 18:
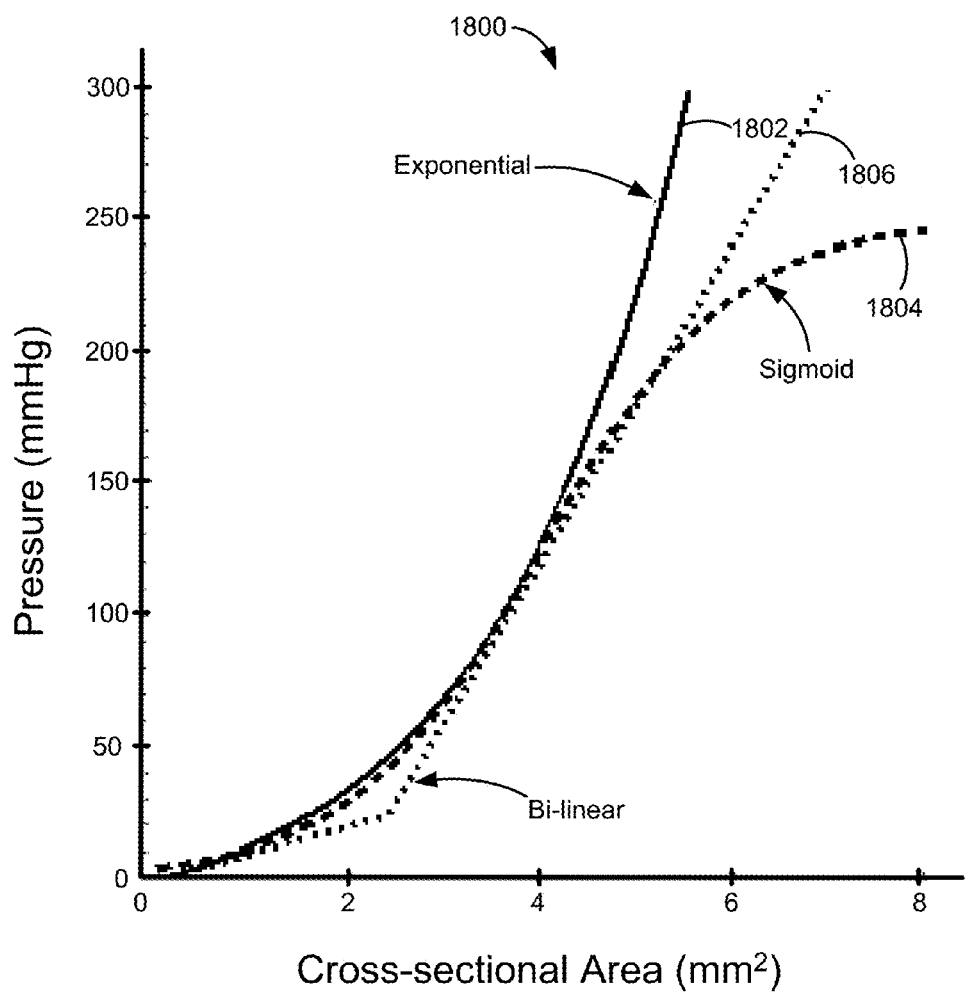
FIG. 18 shows plots of example transmural blood pressure curves as functions of the cross-sectional area of an artery based on three different models.

Although the implementations described in detail above with respect to many of equations 1-6 and 8-14 were described in the context of a stress-strain relationship in which the transmural blood pressure P is modeled as an exponential function of the cross-sectional area A of an artery, some other implementations can utilize other models for representing the stress-strain relationship. For example, in some other implementations, the stress-strain relationship can be modeled as a bilinear relationship, a sigmoid relationship or an arctan relationship between the transmural blood pressure P and the cross-sectional area A of the artery. FIG. 18 shows plots 1800 of example transmural blood pressure curves as functions of the cross-sectional area of an artery based on three different models. For example, the plot 1802 shows a relationship between transmural blood pressure P and cross-sectional area A of an artery based on an exponential model as described above. The plot 1804 shows a relationship between transmural blood pressure P and cross-sectional area A of an artery based on a sigmoid model. The plot 1806 shows a relationship between transmural blood pressure P and cross-sectional area A of an artery based on a bilinear model. In some such implementations utilizing different stress-strain relationships, the relationship between the transmural blood pressure P and the cross-sectional area A can again be inverted to express the area A as a function of the pressure P. The inverted relationship can then be substituted into the approximated Bramwell-Hill equation shown in equation 5 and analytically or numerically solved to express the transmural blood pressure P as a function of PWV.

Additionally, in some other implementations, the stress-strain relationship (regardless of the particular model utilized) can be substituted into a different equation than the Bramwell-Hill equation shown in equation 3. For example, in some other implementations, the stress-strain relationship can be expressed as a function of the elasticity (or inversely the stiffness) of the arterial walls of an artery and substituted into the Moens-Kortewig equation, shown in equation 15 below, which models PWV as a function of the incremental elastic modulus of the arterial wall (an indicator of the wall's "distensibility").

$$PWV = \sqrt{\frac{E_{inc}w}{2r\rho}} \quad (15)$$

In equation 15, $E_{inc}$ is the incremental elastic modulus of the arterial wall, w is the wall thickness and r is the radius of the artery. As a person of ordinary skill in the art will appreciate, the Moens-Kortewig equation can be derived from the Bramwell-Hill equation, and vice versa.

Estimating Pulse Pressure from PWV and Distension

In some implementations, the pulse pressure δP in equation 5, can be expressed as follows in equation 16.

$$\delta P = c_h * \delta A / A \quad (16)$$

where $c_h$ is again a reference to the product of the blood density ρ and the square of the PWV at the reference level h (for example, heart level). The distension δA may be measured as a part of the arterial distension data measurements obtained by the arterial distension sensors (for example, sensors 406 and 408). For example, the controller 412 can determine the distension δA as the amplitude of the arterial distension data signals obtained by the first and the second arterial distension sensors 406 and 408. However, the mean cross-sectional area ⟨A⟩ also is needed. The mean signal amplitude at different elevations can be sufficient. However, arterial distension sensors such as IPG and PPG devices will in general provide an output containing a slowly-varying bias term. This bias term may be caused by the filling or draining of arteries close to the artery being probed. In such cases, the cross-sectional area may be retrieved from the pulse shape, for example, the diastolic part will often exhibit an exponential decay with an asymptotic value, and the area A corresponding to the asymptotic pressure value can be taken as the mean cross-sectional area ⟨A⟩.

However, some ultrasound- and optical-based arterial distension sensors can enable the retrieval of the cross-sectional area A jointly with the distension δA, which would solve the problem. An alternative scheme exclusively based on measuring PWV, distension δA, and elevation (heights) can be obtained. For example, the difference ΔA of the mean arterial cross-sections A at two different elevations can be evaluated on the basis of equation 2. Performing a series expansion with one term yields equation 17 below, $$\Delta A \cong A_0 \frac{\Delta P}{2(\langle P \rangle + P_0)}, \quad (17)$$

where $\langle P \rangle \equiv (P_1 + P_2)/2$.

CONCLUSION

Various modifications to the implementations described in this disclosure may be readily apparent to those skilled in the art, and the generic principles defined herein may be applied to other implementations without departing from the spirit or scope of this disclosure. Thus, the following claims are not intended to be limited to the implementations shown herein, but are to be accorded the widest scope consistent with this disclosure, the principles and the novel features disclosed herein.

Additionally, certain features that are described in this specification in the context of separate implementations also can be implemented in combination in a single implementation. Conversely, various features that are described in the context of a single implementation also can be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Further, the drawings may schematically depict one more example processes in the form of a flow diagram. However, other operations that are not depicted can be incorporated in the example processes that are schematically illustrated. For example, one or more additional operations can be performed before, after, simultaneously, or between any of the illustrated operations. Moreover, various ones of the described and illustrated operations can itself include and collectively refer to a number of sub-operations. For example, each of the operations described above can itself involve the execution of a process or algorithm. Furthermore, various ones of the described and illustrated operations can be combined or performed in parallel in some implementations. Similarly, the separation of various system components in the implementations described above should not be understood as requiring such separation in all implementations. As such, other implementations are within the scope of the following claims. In some cases, the actions recited in the claims can be performed in a different order and still achieve desirable results.

What is claimed is:

1. A device capable of estimating blood pressure comprising:
   two or more sensors capable of performing measurements along an artery of a subject; and
   at least one processing unit coupled with the two or more sensors and capable of:
     accessing one or more parameters including a stress-strain parameter based on a hydrostatic pressure calibration;
     determining a pulse transit time (PTT) of a pulse propagating in the artery based on the measurements performed by the two or more sensors, the PTT being a time during which the pulse propagates from a first physical location to a second physical location;
     determining a pulse wave velocity (PWV) based on the PTT; and
     determining a blood pressure in the artery based on the PWV and the stress-strain parameter.

2. The device of claim 1, wherein the two or more sensors include at least a first sensor positioned at the first physical location and a second sensor positioned at the second physical location, and wherein the determination of the PTT based on the measurements performed by the two or more sensors includes:
   determining a first temporal location of a pulse propagating through the artery based on the measurements performed by the first sensor;
   determining a second temporal location of the pulse based on the measurements performed by the second sensor; and
   determining the PTT based on the first temporal location and the second temporal location.

3. The device of claim 2, further including a wearable housing that encompasses at least portions of the first sensor and the second sensor, the wearable housing providing a fixed distance of separation between the first sensor and the second sensor, the processing unit being capable of determining the PWV based on the fixed distance of separation and the PTT.

4. The device of claim 3, wherein a magnitude of the fixed distance of separation is less than about 5 centimeters (cm).

5. The device of claim 1, wherein the determination of the blood pressure in the artery based on the PWV and the stress-strain parameter includes determining the blood pressure based on a first relationship between blood pressure and PWV that includes the stress-strain parameter and no other stress-strain parameters.

6. The device of claim 1, wherein the at least one processing unit is capable of performing the hydrostatic pressure calibration to obtain the stress-strain parameter.

7. The device of claim 6, further including at least one elevation sensor coupled with the at least one processing unit and capable of performing elevation measurements associated with a relative or an absolute elevation of the device, the at least one processing unit being capable of determining the stress-strain parameter based on a hydrostatic pressure difference between a first elevation and a second elevation.

8. The device of claim 1, further including a signal processor capable of performing one or more signal processing operations on the measurements performed by the two or more sensors to provide processed arterial distension data.

9. The device of claim 8, wherein one or more of the one or more signal processing operations includes applying a nonlinear function to provide the processed arterial distension data.

10. The device of claim 1, wherein the determination of the PTT based on the measurements performed by the two or more sensors comprises:
   performing a correlation operation based on the measurements performed by a first sensor at a first physical location and based on the measurements performed by a second sensor at a second physical location;
   determining correlation data as a function of time delay based on the correlation operation;
   determining a time delay associated with an approximate maximum of the correlation data; and
   determining the PTT based on the determined time delay.

11. A device capable of estimating blood pressure comprising:
   one or more sensors capable of performing measurements along an artery of a subject; and
   at least one processing unit coupled to the one or more sensors and capable of:
     accessing one or more parameters including a stress-strain parameter based on a hydrostatic pressure calibration;

determining a blood flow through the artery based on the measurements from the one or more sensors;
determining a cross-sectional area of the artery based on the measurements from the one or more sensors;
determining a pulse wave velocity (PWV) based on the blood flow and the cross-sectional area, the PWV being a velocity at which an arterial distension waveform envelope propagates; and
determining a blood pressure in the artery based on the PWV and the stress-strain parameter.

12. The device of claim 11, wherein the determination of the PWV based on the blood flow and the cross-sectional area includes determining a derivative estimate of the blood flow as a function of the cross-sectional area.

13. The device of claim 12, wherein the determination of the PWV based on the blood flow and the cross-sectional area further includes determining a value of a constant portion of the derivative estimate.

14. A method of estimating blood pressure comprising:
performing measurements of arterial distension by two or more sensors positioned along an artery of a subject;
determining a pulse transit time (PTT) of a pulse propagating in the artery based on the measurements, the PTT being a time during which the pulse propagates from a first physical location to a second physical location;
determining a pulse wave velocity (PWV) based on the PTT; and
accessing one or more parameters including a stress-strain parameter based on a hydrostatic pressure calibration;
determining a blood pressure in the artery based on the PWV and the stress-strain parameter.

15. The method of claim 14, wherein the two or more sensors include at least a first sensor positioned at the first physical location and a second sensor positioned at the second physical location, and wherein determining the PTT based on the measurements performed by the two or more sensors includes:
determining a first temporal location of a pulse propagating through the artery based on the measurements performed by the first sensor;
determining a second temporal location of the pulse based on the measurements performed by the second sensor; and
determining the PTT based on the first temporal location and the second temporal location.

16. The method of claim 15, wherein the first sensor and the second sensor are encompassed at least partially by a wearable housing, the wearable housing providing a fixed distance of separation between the first sensor and the second sensor, and wherein the determining of the PWV is based further on the fixed distance of separation.

17. The method of claim 14, wherein determining the blood pressure in the artery based on the PWV and the stress-strain parameter includes determining the blood pressure based on a first relationship between blood pressure and PWV that includes the stress-strain parameter and no other stress-strain parameters.

18. The method of claim 14, further including performing the hydrostatic pressure calibration to obtain the stress-strain parameter.

19. The method of claim 18, further including:
performing elevation measurements associated with a relative or an absolute elevation; and
determining the stress-strain parameter based on a hydrostatic pressure difference between a first elevation and a second elevation.

20. The method of claim 14, further including applying a nonlinear function to the measurements performed by the two or more sensors to provide processed arterial distension data.

21. The method of claim 14, wherein the determining of the PTT based on the measurements performed by the two or more sensors comprises:
performing a correlation operation based on the measurements performed by a first sensor at a first physical location and based on the measurements performed by a second sensor at a second physical location;
determining correlation data as a function of time delay based on the correlation operation;
determining a time delay associated with an approximate maximum of the correlation data; and
determining the PTT based on the determined time delay.

22. A method of estimating blood pressure comprising:
performing measurements of arterial distension by one or more sensors positioned along an artery of a subject;
determining a blood flow through the artery based on the measurements;
determining a cross-sectional area of the artery based on the measurements;
determining a pulse wave velocity (PWV) based on the blood flow and the cross-sectional area, the PWV being a velocity at which an arterial distension waveform envelope propagates;
accessing one or more parameters including a stress-strain parameter based on a hydrostatic pressure calibration; and
determining a blood pressure in the artery based on the PWV and the stress-strain parameter.

23. The method of claim 22, wherein the determining of the PWV based on the blood flow and the cross-sectional area includes determining a derivative estimate of the blood flow as a function of the cross-sectional area.

24. The method of claim 23, wherein the determining of the PWV based on the blood flow and the cross-sectional area further includes determining a value of a constant portion of the derivative estimate.

* * * * *